(12) United States Patent
Kopka et al.

(10) Patent No.: US 8,440,841 B2
(45) Date of Patent: May 14, 2013

(54) 5-PYRROLIDINYLSULFONYL ISATIN DERIVATIVES

(75) Inventors: Klaus Kopka, Münster (DE); Bodo Levkau, Münster (DE); Michael Schäfers, Havixbeck (DE)

(73) Assignee: Universitätsklinikum Münster, Münster (DE)

( * ) Notice: Subject to any disclaimer, the term of this patent is extended or adjusted under 35 U.S.C. 154(b) by 308 days.

(21) Appl. No.: 11/794,878

(22) PCT Filed: Dec. 22, 2005

(86) PCT No.: PCT/EP2005/013908
§ 371 (c)(1), (2), (4) Date: Feb. 15, 2008

(87) PCT Pub. No.: WO2006/074799
PCT Pub. Date: Jul. 20, 2006

(65) Prior Publication Data
US 2009/0041664 A1     Feb. 12, 2009

(30) Foreign Application Priority Data
Jan. 17, 2005  (EP) .................................. 05000828

(51) Int. Cl.
C09B 5/00      (2006.01)
(52) U.S. Cl.
USPC .......................... 548/416; 514/408; 424/1.65
(58) Field of Classification Search ................. 548/416; 514/408; 424/1.65
See application file for complete search history.

(56) References Cited

U.S. PATENT DOCUMENTS

2004/0167069 A1   8/2004   Khosla et al. .................. 514/12
2006/0275215 A1 * 12/2006  Hiscock et al. ............. 424/1.69

FOREIGN PATENT DOCUMENTS

| WO | WO 99/65451 | 12/1999 |
| WO | WO 01/22966 | 4/2001 |
| WO | WO 2004/062578 | 7/2004 |
| WO | WO 2005/053752 | 6/2005 |

OTHER PUBLICATIONS

Abstract of Kislitsyn, RU 2,232,809; Jul. 2004.*
Methot (J Biol Chem 279, 27905-27914, 2004).*
Bolton, R. (Journal of Labelled Compounds & Radiopharmaceuticals 45(6), 485-528, 2002).*
Podichetty Anil K (J. Med. Chem. 52(11), 3484-95, 2009).*
Chu (J. Med. Chem. 48, 7637, 2005).*
Lahort, Eur. J. Nuc. Med. Mol. Imaging 31(6), 887-919, 2004.*
Lee, et al, "Potent and Selective Nonpeptide Inhibitors of Caspases 3 and 7," Journal of Medical Chemistry (2001), 44, pp. 2015-2026.
Lee, et al, "Potent and Selective Nonpeptide Inhibitors of Caspases 3 and 7 Inhibit Apoptosis and Maintain Cell Functionality," Journal of Biological Chemistry, vol. 275, No. 21, (2000), pp. 16007-16014.

* cited by examiner

*Primary Examiner* — David Lukton
(74) *Attorney, Agent, or Firm* — Kagan Binder, PLLC

(57) ABSTRACT

The present invention relates to novel 5-pyrrolidinylsulfonyl isatin derivatives, non-peptidyl Caspase binding Radioligands (CbRs) and CbR-transporter conjugates derived from said isatin derivatives, diagnostic compositions comprising said compounds of the invention and their use for non-invasive diagnostic imaging.

3 Claims, 3 Drawing Sheets

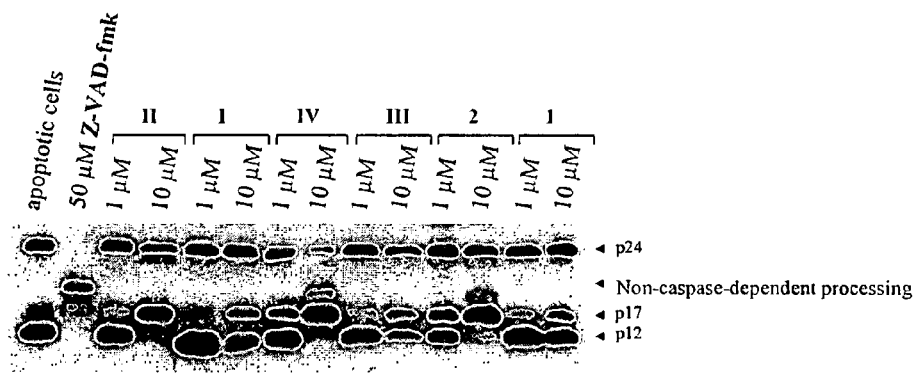

Fig. 1 Western blot analysis of active caspase-3 in apoptotically dying human endothelial cells in the presence of different concentrations (c = 1µM / c = 10µM) of PET- (cpds. II, I, IV, III) and SPECT-compatible (cpds. 2, 1) nonradioactive conterparts of the CbRs. The methoxymethyl compounds II, IV, and 2 inhibit caspase processing to its p12 subunit with compensatory accumulation of the p17 subunit at 10 µM. Z-VAD-fmk is used as a control for full inhibition of caspase processing.

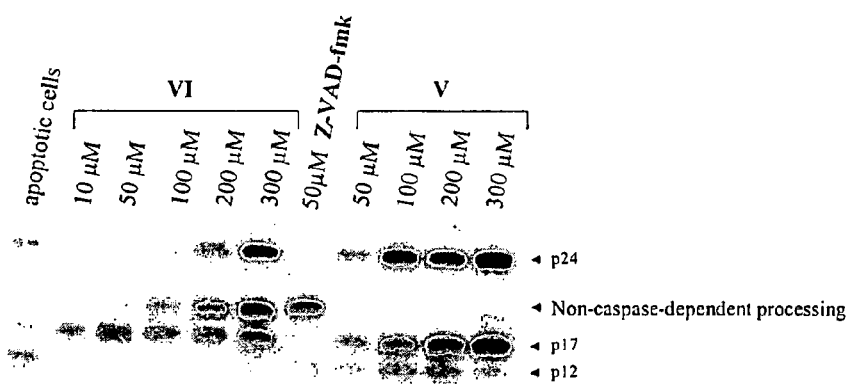
Fig. 2 Western blot analysis of active caspase-3 in apoptotically dying human endothelial cells in the presence of different concentrations (c = 1-300 µM) of fluorinated PET- compatible nonradioactive conterparts of the CbRs VI and V. Inhibition of caspase processing by compound VI occurs at 10

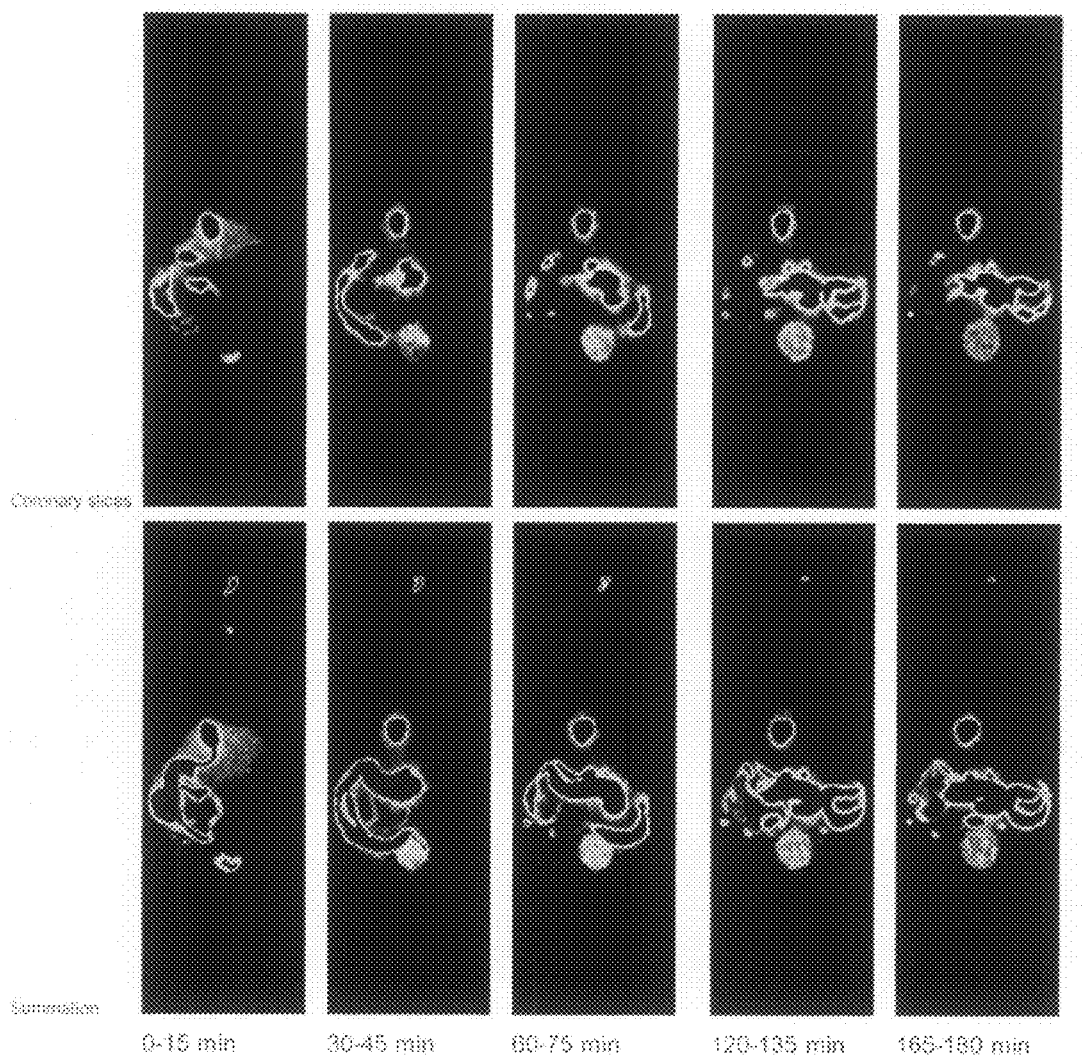
Fig. 3  Examination of the in vivo biodistribution behavior of [$^{18}$F]VI in NMRI athymic nude mice (nu/nu) using the quadHIDAC small-animal PET scanner (scanning time: 180 min after i.v. injection of 7 MBq [$^{18}$F]VI). All organs are cleared from radioactivity after 3 h except the bowels and the gall bladder.

5-PYRROLIDINYLSULFONYL ISATIN DERIVATIVES

This application is a 371 of PCT/EP05/13908, filed Dec. 22, 2005, which claims foreign priority to EP 05000828.3, filed Jan. 17, 2005.

The present invention relates to novel 5-pyrrolidinylsulfonyl isatin derivatives, non-peptidyl caspase binding radioligands (CbR) and CbR-transporter conjugates derived from said isatin derivatives, diagnostic compositions comprising said non-peptidyl CbR and CbR-transporter conjugates of the invention and their use for non invasive diagnostic imaging.

The present invention relates to the establishment of a non-invasive molecular imaging technique for the molecular imaging of caspase activity in vivo. More particularly the inventions pertain to targeting intracellularly the apoptotic process with non-peptidyl imaging agents (namely radiolabeled non-peptidyl caspase inhibitors) that specifically bind to activated caspases (cysteinyl aspartate-specific proteases). In the following these new imaging agents are called CbRs which stands for Caspase binding Radioligands. In addition, to actively translocate the CbRs into cells the principle of molecular transporter conjugates is applied [1-5].

The caspases belong to an enzyme class that play a critical role in the execution of the programmed cell death (apoptosis). Thus, this in vivo target offers the feasibility to diagnose directly diseases (e.g. atherosclerosis, acute myocardial infarction, chronic heart failure, allograft rejection, stroke, neurodegenerative disorders etc.) and/or therapeutic responses (induction of apoptosis in tumors etc.) that correlate immediately with the apoptotic process. The here presented invention can be directly applied in non-invasive nuclear medicinal diagnosis with high clinical impact to differentiate between balanced (physiological) and unbalanced (pathological) apoptosis using Single Photon Emission Computed Tomography (SPECT) or Positron Emission Tomography (PET). In contrast to the known radiolabeled AnnexinV radiotracers that bind to negatively charged phospholipids (especially to phosphatidylserine residues) and therefore are not exclusive markers for apoptosis [6-15], the here described CbRs and CbR-transporter conjugates should be capable to directly target apoptosis in vivo in human beings as imaging agents thereby excluding the imaging of necrotic processes. Consequently, the CbRs and CbR-transporter conjugates could enhance the effectiveness and accuracy of therapeutic interventions in the clinics and offer improved perspectives for the disease management in a variety of clinical disciplines.

BACKGROUND ART

Known potent peptide caspase inhibitors (e.g. the irreversible pan-caspase inhibitor Z-VAD-fmk) [1,6] are only moderately selective and possess only poor cell permeabilities hindering the intracellular targeting of activated caspases [1,7]. In contrast, the 5-pyrrolidinylsulfonyl isatins represent a rare class of non-peptidyl caspase inhibitors which bind selectively to the downstream caspases, preferably to the effector caspases 3 and 7 [19]. The dicarbonyl functionality of the isatins bind in a tetrahedral manner to the caspase active site. A thiohemiketal is formed via the electrophilic C-3 carbonyl of the isatin and the nucleophilic thiolate function of the Cys163 residue of the enzyme. Consequently, the ability of the caspases to cleave substrates possessing a P1 Asp residue that reaches into the primary S1 pocket is blocked (reversible inhibitory effect) [20]. In contrast to the peptidomimetic caspase inhibitors, the 5-pyrrolidinylsulfonyl isatins do not possess an acidic functionality which may bind in the primary Asp binding pocket. Various N-substituted 5-pyrrolidinylsulfonyl isatins with the general formula 1 have been synthesized and disclosed so far [20-22]. Compounds bearing an allyl-, cyclohexylalkyl- or arylalkyl substituent at the N-1 nitrogen of the isatin are highly affine caspase 3 and 7 inhibiting agents. Their potency was proved by in vitro inhibition of recombinant human caspase 3 and 7 using standard fluorometric assays [21]. As recently described a non-peptidyl 5-pyrrolidinylsulfonyl isatin derivative was shown to possess cardioprotective potential in isolated rabbit hearts after ischemic injury as well as in cardiomyocytes [17].

DESCRIPTION OF THE INVENTION

The present invention deals with the in vivo imaging of caspases using the synthetic biomarkers CbR as imaging probes. The caspases represent a family of intracellularly activated enzymes that could be targeted by 5-pyrrolidinylsulfonyl isatins, a class of non-peptidyl caspase inhibitors with high caspase affinity and moderate lipophilicity which implies a potent cell permeability. In addition, CbR-transporter conjugates are intended to improve the translocation of the CbRs into the cells and to advance their target specificity [1-5]. Within the scope of the invention chemically modified and radiolabeled 5-pyrrolidinylsulfonyl isatins should result in potential non-peptidyl CbR tracers as well as CbR-transporter conjugates that form—after non-invasive application (preferably i.v.)—intracellular enzyme-inhibitor complexes by binding of the directly administered CbR or by binding of CbR released from the administered CbR-transporter conjugate at the enzyme active site. The specifically formed enzyme-CbR complex should be detectable in vivo via the nuclear medicinal techniques Positron Emission Tomography (PET) or Single Photon Emission Computed Tomography (SPECT), respectively [23-24]. For this purpose positron-emitting radioactive metals (e.g. Cu-62, Cu-64, Ga-68, Tc-94m) or non-metals (e.g. C-11, N-13, F-18, Br-76, I-124) for PET application as well as gamma-emitting radioactive metals (e.g. Tc-99m, In-111, In-113m, Ga-67) or halogens (e.g. I-123, I-131, Br-77) for SPECT application have to be introduced into the CbRs. The radiochemical modification of the 5-pyrrolidinylsulfonyl isatins should result in similar or even improved pharmacokinetic characteristics of the CbRs or CbR-transporter conjugates to achieve intracellular caspase targeting. Suitable radionuclides/radiosynthons to be used for the radiolabeling of the isatins are preferably C-11-methyliodide [25] or F-18-fluoride [26-29] for PET and I-123-iodide [30-31] or Tc-99m-chelators for SPECT [32-34] that could be coupled each to the biological tracer resulting in the CbR radiotracers. For first in vitro (e.g. cellular assays) and ex vivo (e.g. autoradiography) pharmacological evaluation studies the relevant radioisotopes C-14 and I-125 can also be used to establish the CbR ligands in vitro. In summary, the development of the here presented CbR tracers and CbR-transporter conjugates offer the realization of the non-invasive in vivo monitoring of the rate and extent of apoptosis.

The skeletal structure in formula 1

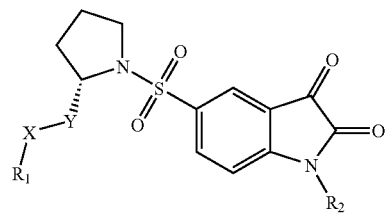

Formula 1: $R_1$-X-Y=e.g. methoxymethyl, phenoxymethyl; $R_2$=e.g. allyl, benzyl, cyclohexylmethyl gives the basis to modify this putative class of non-peptidyl caspase inhibitors by inserting imaging moieties (preferably radionuclides for PET or SPECT) into the residues $R_1$-X-Y and/or $R_2$. In such a way a diagnostic imaging agent for the non-invasive in vivo imaging of apoptosis can be designed.

Preferred synthetic 5-pyrrolidinylsulfonyl isatin caspase inhibitors of the present invention contain substituents as follows:

$R_1$-X-Y=alkyl, heteroalkyl, alkyloxyalkyl, aryloxyalkyl-, alkyloxycarbonyl-, alkylaminoalkyl-, alkylaminocarbonyl-, aryl-, aryloxyalkyl-, arylthioalkyl-, heteroaryl-, arylaminoalkyl-, arylaminocarbonyl- (all of the substituents $R_1$-X-Y can be radiolabeled with PET or SPECT radionuclides and can contain spacers or linkers like PEG, oligopeptides, polyamides, polysaccharides, —NH—$(CH_2)_n$—NH—, —O—$(CH_2)_n$—O— or succinidyl units etc.)

$R_2$=alkyl-, heteroalkyl, allyl- (e.g. fluoroallyl-), aryl-, arylalkyl- (e.g. benzyl -), heteroarylalkyl- (e.g. pyridylmethyl-, picolyl-), alkyloxycarbonylmethyl-, aryloxycarbonylmethyl, Tc-chelators, Ga-chelators (all of the substituents $R_2$ can be radiolabeled with PET or SPECT radionuclides and can contain spacers or linkers like PEG, oligopeptides, polyamides, polysaccharides, —NH—$(CH_2)_n$—NH—, —O—$(CH_2)_n$—O—, succinidyl or 1,4-disubstituted 1,2,3-triazole units etc.)

In particular the present invention relates to 5-pyrrolidinylsulfonyl isatin derivatives of the formula 1:

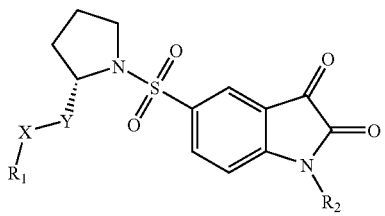

wherein,

X=—O—, —S—, —NH— and Y=$CH_2$—, —C(O)—

$R_1$ is an alkyl group such as methyl, ethyl, or propyl; a substituted alkyl group such as trifluoromethyl, 2-fluoroethyl, 3-fluoropropyl; an aryl group such as phenyl, 4-fluorophenyl or 4-iodophenyl; a heteroarylalkyl group such as 4-picolyl-, 3-picolyl, 2-picolyl-; 6-fluoro-2-picolyl- (=6-fluoropyridyl-2-methyl), 2- or 6-fluoro-3-picolyl (=2- or 6-fluoropyridyl-3-methyl), 2-fluoro-4-picolyl (=2-fluoropyridyl-4-methyl), and optionally additionally comprises a spacer or linker selected from $PEG_{1-200}$, oligopeptide, polyamide, polysaccharide, —NHC(O)—$((CH_2)_n$—NH—C(O))$_m$—, —O—$((CH_2)_n$—O)$_m$—, succinyl and 1,4-disubstituted 1,2,3-triazole units, wherein n=0-6 and m=1-200;

$R_2$ is an optionally substituted alkyl, heteroalkyl, aralkyl, heteroarylalkyl carboxymethyl or methyloxycarbonylmethyl group, wherein the substituents are selected from F, I, Br, OH, $NH_2$, methylamino, isopropylamino, methoxy, fluoroethyloxy, fluoropropyloxy, trimethylamino, nitro, tosylate, triflate, mesylate, diazonium —$N_2^+$, 3-fluorobenzoyl, 4-fluorobenzoyl, 4-fluorophenyl, tributylstannyl, trimethylstannyl, trimethylsilyl and 2-hydrazino-pyridin-5-carbonyl, such as methyl, ethyl, propyl, allyl, cyclohexylmethyl, 2-aminoethyl, 3-aminopropyl, 2-methylaminoethyl, 3-methylaminopropyl, 2-hydroxyethyl, 3-hydroxypropyl, 2-fluoroethyl, 3-fluoropropyl, 2- or 3-fluoroallyl, benzyl, 4-benzyloxybenzyl, 4-fluorobenzyl, 4-(2-fluoroethyloxy)benzyl, 4-(3-fluoropropyloxy)benzyl, 4-hydroxybenzyl, 4-iodobenzyl, 4-methoxybenzyl, piperazin-1-carbonylmethyl, 4-methyl-piperazin-1-carbonylmethyl, 4-isopropyl-piperazin-1-carbonylmethyl, 4-(3-fluoropropyl)piperazin-1-carbonylmethyl, 4-picolyl-, 3-picolyl, 2-picolyl-; 6-fluoro-2-picolyl- (=6-fluoropyridyl-2-methyl), 2- or 6-fluoro-3-picolyl (=2- or 6-fluoropyridyl-3-methyl), 2-fluoro-4-picolyl (=2-fluoropyridyl-4-methyl);

or a metal-chelator (e.g. hydrazinonicotinamide HYNIC, histidine, DOTA and DOTA derivatives, $MAG_3$, BAT, DTPA, EDTA, DAD, Pn216, carbaPn216, Pn44 etc.) or a metall-chelator bound to an aralkyl, aminoalkyl, hydroxyalkyl or a piperazin-1-carbonylmethyl group;

and optionally additionally comprises a spacer, linker or molecular transporter selected from AnnexinV, $PEG_{1-200}$, oligopeptide, polyamide, polysaccharide, —NHC(O)—$((CH_2)_n$—NH—C(O))$_m$—, —O—$((CH_2)_n$—O)$_m$—,succinyl and 1,4-disubstituted 1,2,3-triazole units, wherein n=0-6 and m=1-200 and wherein $R_2$ can also contain an amino acid selected from histidine, lysine, tyrosine, cysteine, arginine, aspartic acid (e.g. cysteine as linker or spacer bound to octaarginine (see Scheme 6) or Annexin V (see Scheme 7) in CbR-transporter conjugates; or histidine as chelator in $^{99m}$Tc-labeled CbR (Table 4, $2^{nd}$ example)).

In a preferred embodiment the group $R_1$-X-Y is an alkoxyalkyl, aryloxyalkyl, arylthioalkyl, alkyloxycarbonyl, aryloxycarbonyl or arylaminocarbonyl group.

Furthermore it is preferred that $R_2$ is an aralkyl group or a Tc-, Cu-, Ga- or In -helator or a Tc-, Cu-, Ga- or In-chelator bound to an aralkyl, aminoalkyl, hydroxyalkyl or a piperazin-1-carbonyl group.

Moreover, compounds are preferred, wherein $R_1$-X-Y and/or $R_2$ additionally comprises a spacer, linker or molecular transporter selected from AnnexinV, polyethylene glycol $PEG_{1-200}$, from an oligopeptide (e.g. heptaarginine, octaarginine, homopolyarginine, heteropolyarginine), from a polyamide, from a polysaccharide, —NHC(O)—$((CH_2)_n$—NH—C(O))$_m$—, —O—$((CH_2)_n$—O)$_m$—, succinyl and 1,4-disubstituted 1,2,3-triazole units, wherein n=0-6 and m=1-200.

In a further embodiment the present invention provides non-peptidyl CbRs (Caspase binding Radioligands) having the formula as defined in any one of claims 1 to 4, wherein at least one of the substituents $R_1$-X-Y or $R_2$ is labelled with a positron-emitting metal radionuclide selected from Cu-62, Cu-64, Ga-68 and Tc-94m, a positron-emitting non-metal radionuclide selected from C-11, N-13, F-18, Br-76 and I-124, gamma- and/or beta-emitting metal radionuclide selected from Tc-99m, In-111, In-113m, Ga-67 and Cu-67 and gamma - and or/beta-emitting non-metal radionuclide selected from C-14, I-123, I-125, I-131 and Br-77.

In a preferred embodiment of the CbR the group $R_1$—X—Y is 4-[$^{123}$I]iodophenoxymethyl-, 4-[$^{18}$F]fluorophenoxymethyl-, [$^{18}$F]trifluoromethyloxymethyl-, 2-[$^{18}$F]fluoroethyloxymethyl, 3-[$^{18}$F]fluoropropyloxymethyl, 2-[$^{18}$F]fluoroethyloxycarbonyl, 4-[$^{11}$C]methyloxyphenoxymethyl, or [$^{11}$C]methyloxycarbonyl, and/or $R_2$ is AnnexinV-S-Cys-acyloxybenzyl-, thus forming a phosphatidyl serinopathy-dependent CbR-transporter conjugate (see Scheme 7); $Arg_8$-S-Cys-acyloxybenzyl-(see Scheme 6), thus forming a phosphatidyl serinopathy-independent CbR-transporter conjugate; 3-[$^{123}$I]iodo-4-hydroxybenzyl-, 4-[$^{11}$C]iodobenzyl-, [$^{11}$C]methyl, 3-[$^{11}$C]methylaminopropyl, 3-(2'-[$^{11}$C]isopropyl)aminopropyl, [$^{11}$C]

methyloxycarbonylmethyl, 4-[$^{11}$C]methyloxybenzyl, 4-(2-[$^{18}$F]fluoroethyloxy)benzyl, 4-(3-[$^{18}$F]fluoropropyloxy)benzyl, 4-[$^{11}$C]methyl-piperazin-1-carbonylmethyl, 4-(2'-[$^{11}$C]isopropyl)piperazin-1-carbonylmethyl, 4-(3-[$^{18}$F]fluoropropyl)piperazin-1-carbonylmethyl), 6-[$^{18}$F]fluoro-2-picolyl- (=6-[$^{18}$F]fluoropyridyl-2-methyl), 2- or 6-[$^{18}$F]fluoro-3-picolyl (=2- or 6-[$^{18}$F]fluoropyridyl-3-methyl), 2-[$^{18}$F]fluoro-4-picolyl (=2-[$^{18}$F]fluoropyridyl-4-methyl); [$^{11}$C]methyloxycarbonylmethyl, a $^{99m}$Tc-chelator-group, or a $^{68}$Ga-chelator-group.

Moreover the present inventions provides a diagnostic composition comprising a non-peptidyl CbR (Caspase binding Radioligand) and/or a CbR-transporter conjugate as described above.

In a further embodiment the present invention provides the use of a non-peptidyl CbR and/or a CbR-transporter conjugate as described above for the preparation of a diagnostic composition for non-invasive imaging of caspase activity in vivo by Single Photon Emission Computed Tomography (SPECT) or Positron Emission Tomography (PET) [23-24].

The diagnostic compositions according the present invention in particular be used for the diagnosis of disorders connected with apoptosis and/or monitoring therapeutic responses connected with apoptosis, thus in the diagnosis of atherosclerosis, acute myocardial infarction, chronic heart failure, allograft rejection, stroke or neurodegenerative disorders.

In a further preferred embodiment the diagnostic compositions according the present invention may be used in the monitoring of induction of apoptosis in tumors, in particular for monitoring chemotherapy-induced or ionizing radiation-induced apoptosis.

It will be appreciated by the person of ordinary skill in the art that the present invention also comprises all stereoisomers of the compounds according to the invention, including its enantiomers and diastereomers. Individual stereoisomers of the compounds according to the invention can be substantially present pure of other isomers, in admixture thereof or as racemates or as selected stereoisomers.

The nomenclature of the compound numbering used herein is as follows:

I, II, III, IV, V etc.=non-radioactive reference compounds of PET-compatible CbR tracers or CbR-transporter conjugates

[$^{11}$C]II, [$^{11}$C]III, [$^{18}$F]IV etc.=PET-compatible CbR tracers or CbR-transporter conjugates Ia, Ib, Ic, IIa, IIa, IIb, IIc etc.=precursors of PET-compatible CbR tracers or CbR -transporter conjugates for radiolabeling 1, 2, 3, 4, 5 etc.=non-radioactive reference compounds of SPECT-compatible CbR tracers or CbR-transporter conjugates

[$^{123}$I]1, [$^{123}$I]2, [$^{99m}$Tc]3 etc.=SPECT-compatible CbR tracers or CbR-transporter conjugates 1a, 1b, 1c, 2a, 2b, 2c, 3a, 3b, 3c etc.=precursors of SPECT-compatible CbR tracers or CbR-transporter conjugates for radiolabeling especially: Iaa, Ibb, IIcc etc=intermediates of precursor compounds Ia, 1b, IIc etc.

The caspase 3 and 7 selective isatin sulfonamides (S)-1-methyl-5-(1-[2-(phenoxymethyl)pyrrolidinyl]sulfonyl)isatin I ($K_i$ (Caspase 3)=15 nM) and (S)-5-(1-[2-(methoxymethyl)pyrrolidinyl]-sulfonyl)isatin IIa ($K_i$ (Caspase 3)=60 nM) were chosen as lead structures to develop CbRs (Scheme 1) [20].

Scheme 1: Isatin sulfonamides I and IIa [20] as lead structures for CbR development.

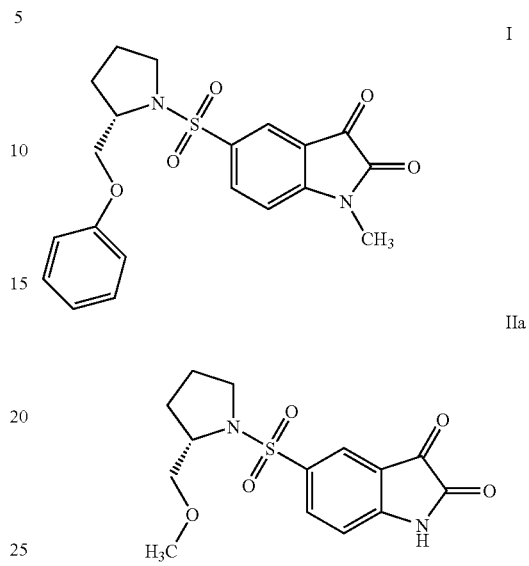

Concerning the here disclosed invention compound IIa is an example of a CbR precursor that could be radiolabeled by C-11-methylation of the N-1 isatin nitrogen resulting in the potential PET-compatible CbR (S)-5-(1-[2-(methoxymethyl) pyrrolidinyl]sulfonyl)-1-[$^{11}$C]methyl-isatin [$^{11}$C]II. Compound I represents the non-radioactive counterpart of a PET-compatible CbR which should be available by authentic radiolabeling (here: again N—[$^{11}$C]methylation) of the desmethyl precursor (S)-5-(1-[2-(phenoxymethyl)pyrrolidinyl] sulfonyl)isatin Ia resulting in the feasible PET-compatible CbR (S)-1-[$^{11}$C]methyl-5-(1-[2-(phenoxymethyl)pyrrolidinyl]sulfonyl)isatin [$^{11}$C]I (Scheme 2).

Scheme 2: Examples of C-11-labeled PET-compatible CbRs.

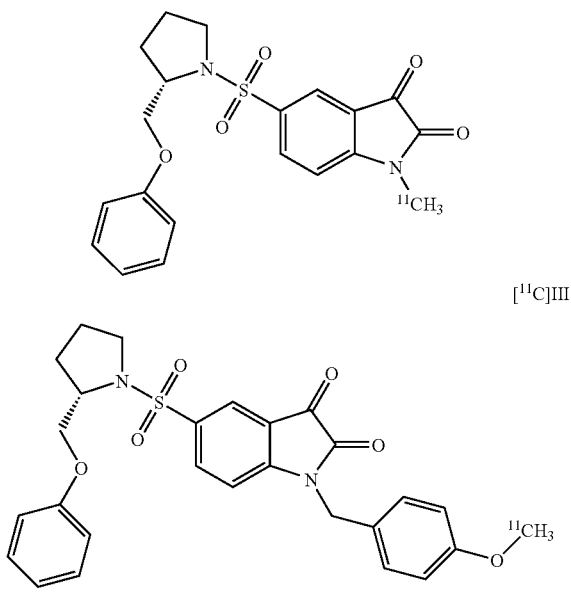

The F-18-fluoroalkylation of the isatin N-1 nitrogen should be also possible (e.g. nucleophilic substitution reaction of a corresponding 3-tosylpropyl precursor with [$^{18}$F]K(Kryptofix222)F). In table 1 further PET-compatible CbRs are summarised that are achievable using the radiosynthons [$^{18}$F]F$_2$, [$^{18}$F]K(Kryptofix222)F, [$^{18}$F]F—(CH$_2$)$_n$-LG (n=1-3, LG=Tos, Hal, Tf, Ms), [$^{11}$C]CH$_3$X (X=I, Tf) or [$^{11}$C]acetone.

TABLE 1

Selection of CbRs for PET, radiolabeled in R$_2$ (LG = Tos, Tf, Ms)

| Lead structure | Precursor R$_2$ = | PET-Tracer R$_2$ = |
|---|---|---|
| (isatin sulfonamide core; R$_1$ = e.g. CH$_3$, CF$_3$, Ph) | H | $^{11}$CH$_3$ |
| | H$_2$C–C(=O)–OH | H$_2$C–C(=O)–O$^{11}$CH$_3$ |
| | H$_2$C–C(=O)–OH | H$_2$C–C(=O)–OCH$_2$CH$_2$$^{18}$F |
| | H$_2$C–CH$_2$–CH$_2$–LG | H$_2$C–CH$_2$–CH$_2$–$^{18}$F |
| | H$_2$C–CH$_2$–CH$_2$–NH$_2$ | H$_2$C–CH$_2$–CH$_2$–NH$^{11}$CH$_3$ |
| | H$_2$C–CH$_2$–CH$_2$–NH$_2$ | H$_2$C–CH$_2$–CH$_2$–NH–$^{11}$CH(CH$_3$)$_2$ |
| | H$_2$C–C(=O)–piperazine-NH | H$_2$C–C(=O)–piperazine-N–$^{11}$CH$_3$ |
| | H$_2$C–C(=O)–piperazine-NH | H$_2$C–C(=O)–piperazine-N–$^{11}$CH(CH$_3$)$_2$ |
| | H$_2$C–C(=O)–piperazine-NH | H$_2$C–C(=O)–piperazine-N–CH$_2$CH$_2$CH$_2$–$^{18}$F |
| | H$_2$C–C$_6$H$_4$–OH | H$_2$C–C$_6$H$_4$–O–CH$_2$CH$_2$–$^{18}$F |
| | H$_2$C–C$_6$H$_4$–OH | H$_2$C–C$_6$H$_4$–O$^{11}$CH$_3$ |
| | H$_2$C–C$_6$H$_4$–O–CH$_2$CH$_2$–LG | H$_2$C–C$_6$H$_4$–O–CH$_2$CH$_2$–$^{18}$F |

TABLE 1-continued
Selection of CbRs for PET, radiolabeled in $R_2$ (LG = Tos, Tf, Ms)
| Lead structure | Precursor $R_2 =$ | PET-Tracer $R_2 =$ |
|---|---|---|
| | 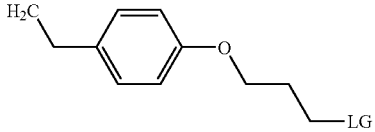 | 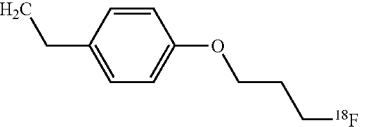 |
| |  | 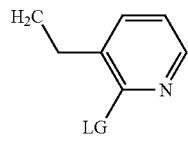 |
| | 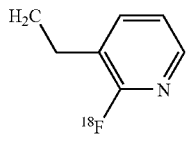 |  |
wherein Tos = tosylate
Tf = triflate
Ms = mesylate
TABLE 2
Selection of CbRs for PET, radiolabeled in $R_1$ (LG = Tos, Tf, Ms)
| Lead structure | Precursor $R_1 =$ | PET-Tracer $R_1 =$ |
|---|---|---|
| 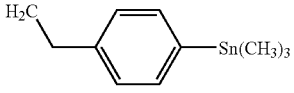<br>$R_2$ = e.g. $CH_3$, allyl, benzyl, picolyl | 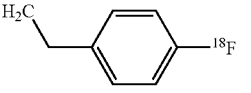 | 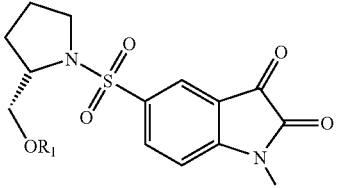 |
| | 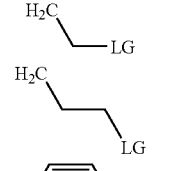 | 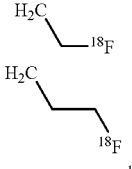 |
| |  | 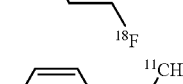 |
| | 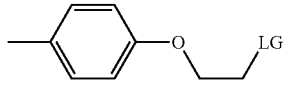 | 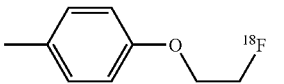 |
| | 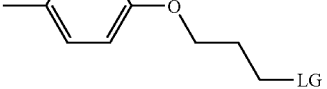 | 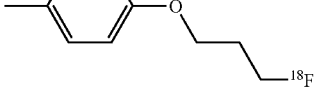 |
| | 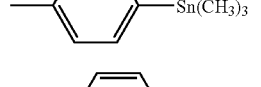 | 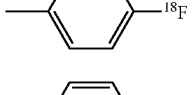 |
| | 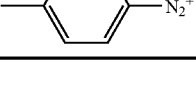 | 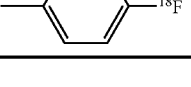 |

In addition to the PET-compatible CbR tracers to be developed especially SPECT-compatible CbR tracers are attractive for commercialisation purposes owing to the somewhat longer lived SPECT nuclides I-123 ($T_{1/2}$=13.2 h) and Tc-99m ($T_{1/2}$=6 h). This circumstance allows professional shipment and distribution of the corresponding CbR tracers as radiopharmaceuticals after realisation of the necessary clinical phase studies regarding the pharmaceutical as well as the radiation protection guidelines. In contrast to C-11-labeled CbR tracers ($T_{1/2}$=20 min), the commercialisation of F-18-labeled ($T_{1/2}$=110 min) and Ga-68-labeled ($T_{1/2}$=67.6 min) CbR ligands would be also possible but is limited to a so called satellite distribution system.

In scheme 3 the I-123-labeled SPECT-compatible CbR tracer (S)-1-(4-[$^{123}$I]iodobenzyl)-5-(1-[2-(phenoxymethyl)pyrrolidinyl]sulfonyl)isatin [$^{123}$I]1 is displayed which is available by iododemetalation reaction [30] of the precursor (S)-5-(1-[2-(phenoxymethyl)pyrrolidinyl]sulfonyl)-1-(4-(tributylstannyl)benzyl)isatin 1a (For the synthesis of non-radioactive SPECT CbR references and radiolabeled SPECT CbR model tracers please see below).

Scheme 3: Example of a I-123-labeled SPECT-compatible CbR [$^{123}$I]1.

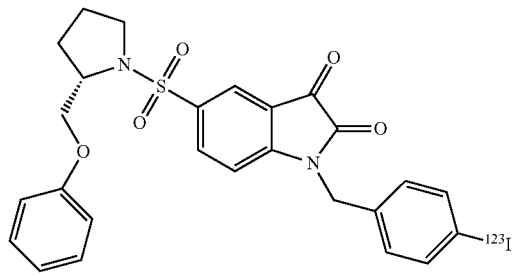

Scheme 4: N-Benzyloxy substituted compounds may be used as lead structures for various radiolabeling strategies.

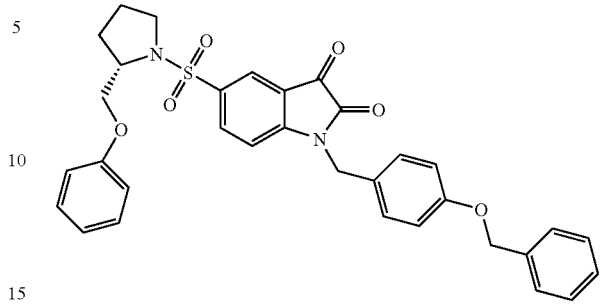

TABLE 3

Selection of I-123-labeled CbRs for SPECT

| Lead structure | Precursor R$_2$ = | SPECT-Tracer R$_2$ = |
|---|---|---|
| $R_1$ = e.g. CH$_3$, CF$_3$, Ph | H$_2$C—⌬—SnBu$_3$ <br> H$_2$C—⌬—OH | H$_2$C—⌬—$^{123}$I <br> H$_2$C—⌬—OH, $^{123}$I |

| Lead structure | Precursor R$_1$ = | SPECT-Tracer R$_1$ = |
|---|---|---|
| $R_2$ = e.g. CH$_3$, CF$_3$, allyl, benzyl, picolyl | —⌬—SnBu$_3$ <br> —⌬—OH | —⌬—$^{123}$I <br> —⌬—OH, $^{123}$I |

Scheme 5: Lead structure for the linkage of feasible Tc-99m-chelators (X = e.g. —NH—, —N—C(=O)—, —C(=O)N—).

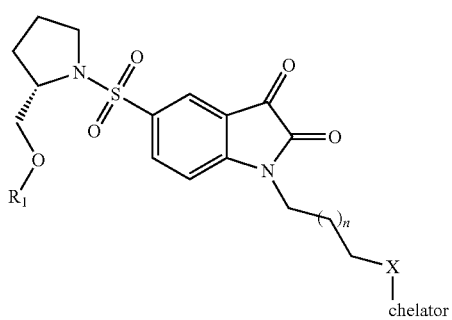

Furthermore, the isatin N-1 nitrogen provides a promising position for the coupling with Tc-99m-chelators to yield potential Tc-99m-technetium CbR tracers. A modified isatin lead structure is suggested in scheme 5 which offers the opportunity to link a variety of Tc-99m-technetium chelates with $N_4$, $N_2O_2$, $N_2S_2$, $N_3S$, $N_3O_3$, $N_2O(CO)_3$ etc. coordination sphere. Examples are given as follows:

All the compounds derived by the chelator modifications (see items 1.-5., below) represent precursors for the radiosyntheses of Tc-99m-SPECT-compatible CbRs which are available via ordinary kit preparation procedures.

Tc-chelators according to the present invention are e.g. the compounds as listed below, however, they are not limited to them [34]:

1.

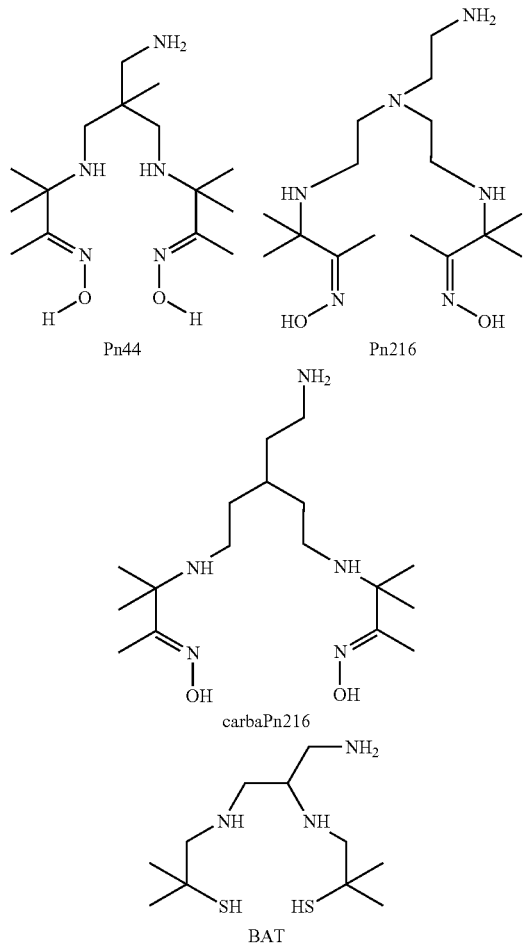

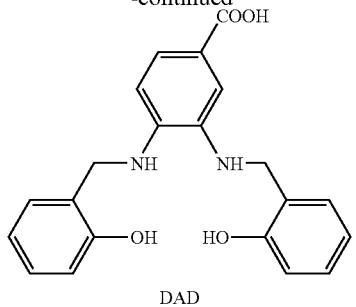

DAD

2. Further chelators according to the present invention are e.g. derivatives of MAG3 (mercapto acetyl triglycine) or tripodand ligands with $N_3S$—, $N_2S_2$-etc. coordination sphere, which could be also linked to the isatin N-1 nitrogen using similar spacers (alkyl, polyethylenglycol (PEG), oligopeptide, polyamide, oligosaccharide spacers etc.) in the manner presented in scheme 5.

3. Moreover, also the chelators Pn44, Pn216, carbaPn216 or BAT or any other suitable chelator with $N_4$—, $N_2O_2$—, $N_2S_2$—, $N_3S$— etc. coordination sphere may be attached to the lead structure by the substitution of the corresponding halogeno isatin derivative via the $NH_2$ residues of the chelators (scheme 5: coupling moiety X=—NH—).

4. Additional chelators that may be used in the present invention are the chelators DAD, MAG3 or any other suitable chelator with $N_4$—, $N_2O_2$—, $N_2S_2$—, $N_3S$— etc. coordination sphere and may be attached to an amino group of a suitable precursor by an amidation reaction (see Scheme 5: coupling moiety X=—N—C(=O)—).

5. Moreover the chelators Pn44, Pn216, carbaPn216 or BAT may be attached to the carboxy group of a suitable precursor by an amidation reaction (scheme 5: coupling moiety X=—C(=O)—N—).

In addition, further SPECT-compatible Tc-99m-labeled CbRs are summarised in table 4 that are achievable by histidine [35] and/or HYNIC chelators [36] attached to the isatin N-1 position via alkyl, polyethylenglycol (PEG), oligopeptide, polyamide and/or oligosaccharide spacers or via the amino group of a suitable precursor by an amidation reaction (see Scheme 5: coupling moiety X=—N—C(=O)—).

TABLE 4

Tc-99m-labeled CbRs for SPECT (Lead structure see Table 1)

Precursor
$R_2 =$

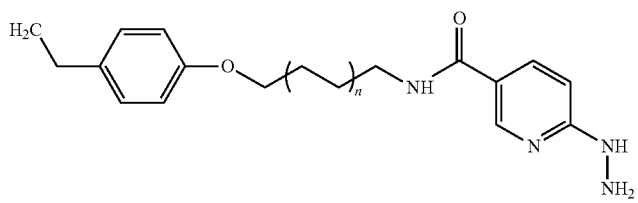

TABLE 4-continued

Tc-99m-labeled CbRs for SPECT (Lead structure see Table 1)

SPECT-Tracer
R$_2$ =

Furthermore, the isatin N-1 nitrogen provides a promising position for the coupling with Ga-68-chelators to yield potential Ga-68-gallium CbR tracers for PET (Table 5).

TABLE 5

Example of a Ga-68-labeled CbR for PET (Lead structure see Table 1)

Precursor
R$_2$ =

PET-Tracer
R$_2$ =

Furthermore, the isatin N-1 nitrogen provides a position for the coupling with molecular transporters like hepta- or octaarginine [1-4] or Annexin V [5] to yield potential CbR-transporter conjugates for SPECT and/or PET.

In a further aspect the present invention provides CbR-transporter conjugates which may be used for an active caspase targeting. Hereby the substituent $R_1$-X-Y of the isatin structure is radiolabeled in contrast to the labeling for the unconjugated CbR wherein particularly the $R_2$ substituent is radiolabeled.

The following SPECT- and PET-compatible $R_1$-X-Y groups are preferred:

4-[$^{123}$I]iodophenoxymethyl-,
4-[$^{18}$F]fluorophenoxymethyl-,
2-[$^{18}$F]fluoroethyloxymethyl,
3-[$^{18}$F]fluoropropyloxymethyl,
2-[$^{18}$F]fluoroethyloxycarbonyl,
[$^{11}$C]methyloxycarbonyl The CbR-transporter conjugates according to the present invention, i.e. the linking of suitably radiolabeled CbRs with so-called molecular transporters may be used to introduce the CbR actively into the cells.

The CbR is linked via the N-1 nitrogen atom of the isatin structure. The CbR-transporter conjugates according the present invention will release the CbR after intracellular intake via cleavage or due to lysosomal degradation of the molecular transporter and thus finally binds to the caspases.

By this implementation of the releasable drug-transporter conjugate approach as described by Wender et al. [1-4], a profound enhancement of sensitivity of caspase detection can be obtained due to the active transport via the membrane into the cells thus also providing an improved apoptosis imaging.

Heteropolyarginines
Homopolyarginines

Targeted drug delivery using the CbRs according to the present invention can be distinguished between:

A phosphatidyl serinopathy-independent transport of the CbR-polyarginine conjugate,
B phosphatidyl serinopathy-dependent transport of the CbR-AnnexinV conjugate.
C dual specificity probes for the detection of apoptosis.

Synthesis of Phosphatidyl Serinopathy-Independent CbR-Polyarginine Conjugates.

Two different species of CbR-transporter-conjugates are synthesized according to the present invention.

A CbR-octaarginine conjugate which may optionally be labeled at the $R_1$ group with [$^{11}$C] or [$^{18}$F] (PET-Tracer) or with [$^{231}$I] (SPECT-Tracer).

This is exemplified in scheme 6 for a [$^{18}$F]-labeled target conjugate, using a modified Balz-Schiemann-Reaktion for the [$^{18}$F]-fluorination labeling [28-29]. A [$^{123}$I]-labeling can be achieved via a tributylstannyl intermediate [31].

Moreover a nitro moiety can be introduced into the phenoxyprolinol of the group $R_1$-X-Y to prepare a subsequent reduction, diazotisation and subsequent [$^{18}$F]-fluorination. In a further embodiment a $R_1$-X-Y tosylate intermediate (e.g. $R_1$-X -Y=3-tosylpropyloxymethyl) can be [$^{18}$F]fluorinated with [$^{18}$F]K(Kryptofix222)F (see Table 6, $R_1$-X-Y=3-[$^{18}$F]fluoropropyloxymethyl). The modification of the isatin-nitrogen substituent can be achieved via a protected p-hydroxy-benzylfunction and the molecular transporter such as octaarginine, can be bound to the CbR via a modified cysteine-bridge.

TABLE 6

Selection of radiolabeled CbR-transporter conjugates for SPECT or PET

| Lead structure | $R_1$—X—Y = | $R_2$ = |
|---|---|---|
| | PET | |
| | [$^{18}$F]F(CH$_2$)$_2$OCH$_2$ | Arg$_8$-S-Cys-acyloxybenzyl |
| | [$^{18}$F]F(CH$_2$)$_3$OCH$_2$ | " |
| | 4-[$^{18}$F]F—C$_6$H$_4$—OCH$_2$ | " |
| | [$^{18}$F]F(CH$_2$)$_2$OCO | " |
| | [$^{11}$C]CH$_3$OCO | " |
| | [$^{18}$F]F(CH$_2$)$_2$OCH$_2$ | AnnexinV-S-Cys-acyloxybenzyl |
| | [$^{18}$F]F(CH$_2$)$_3$OCH$_2$ | " |
| | 4-[$^{18}$F]F—C$_6$H$_4$—OCH$_2$ | " |
| | [$^{18}$F]F(CH$_2$)$_2$OCO | " |
| | [$^{11}$C]CH$_3$OCO | " |
| | CH$_3$OCH$_2$ | $^{68}$Ga-AnnexinV-S-Cys-acyloxybenzyl |
| | C$_6$H$_5$OCH$_2$ | " |
| | CH$_3$OCH$_3$ | $^{18}$F-AnnexinV-S-Cys-acyloxybenzyl |
| | C$_6$H$_5$OCH$_2$ | " |
| | SPECT | |
| | 4-[$^{123}$I]I—C$_6$H$_4$—OCH$_2$ | Arg$_8$-S-Cys-acyloxybenzyl |
| | 4-[$^{123}$I]I—C$_6$H$_4$—OCH$_3$ | AnnexinV-S-Cys-acyloxybenzyl |
| | CH$_3$OCH$_2$ | $^{99m}$Tc-AnnexinV-S-Cys-acyloxybenzyl |
| | C$_6$H$_5$OCH$_2$ | " |
| | CH$_3$OCH$_3$ | $^{123}$I-AnnexinV-S-Cys-acyloxybenzyl |
| | C$_6$H$_5$OCH$_2$ | " |

As molecular transporters according to the present invention the following may be used:

Annexin V
Heptaarginine
Oktaarginine

Various substituents R (see Scheme 6) can be used to obtain different in vitro und in vivo-stabilities of the conjugate.

Depending on the nature of R CbR is released by an intramolecular substitution within minutes to several hours, whereby the active ingredient acts as a leaving group [1-2].

The last 5 steps of the synthesis beginning with the [$^{18}$F]-labeling are carried out with an automated synthesis module.
Scheme 6 Synthesis of a [$^{18}$F]-labeled CbR-octaarginine conjugate
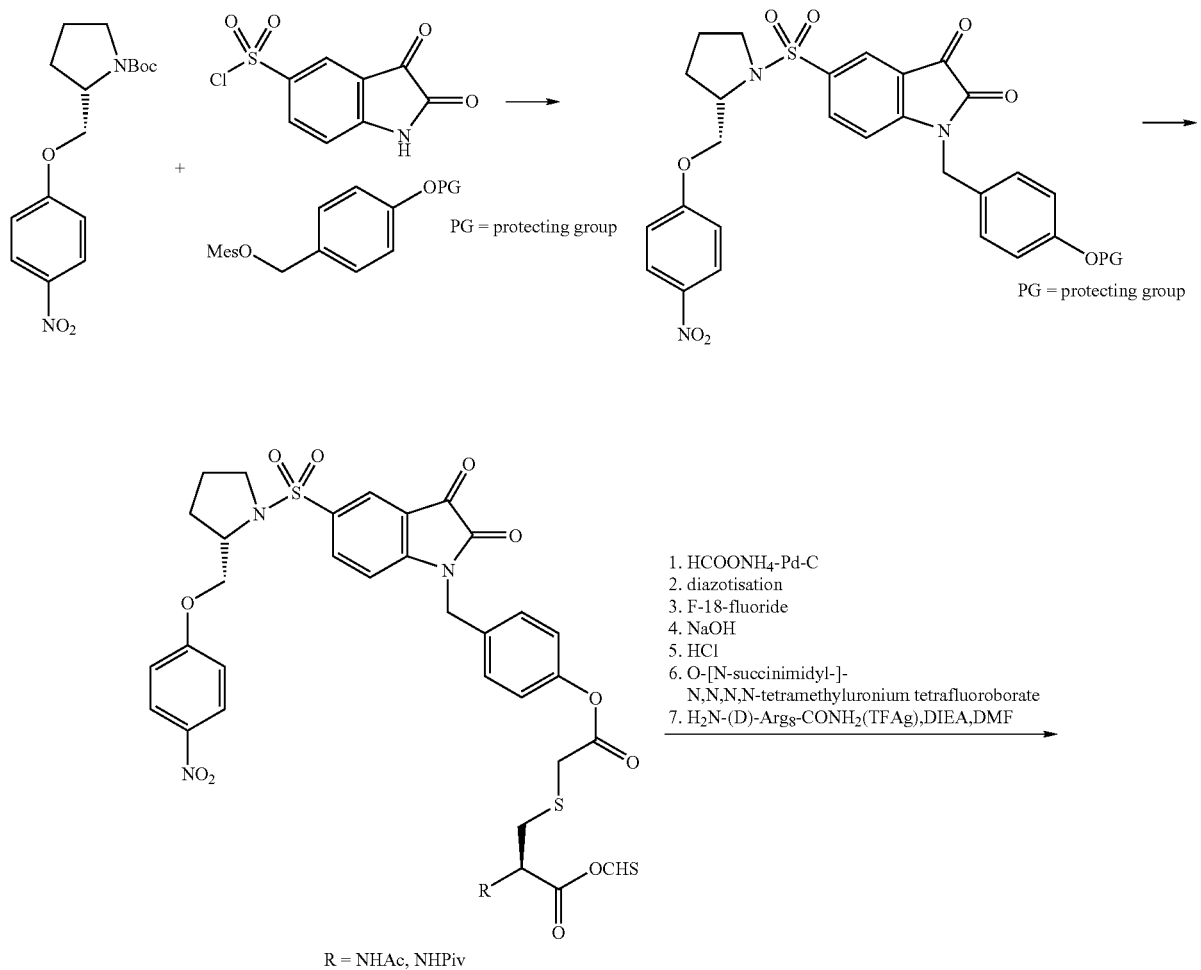
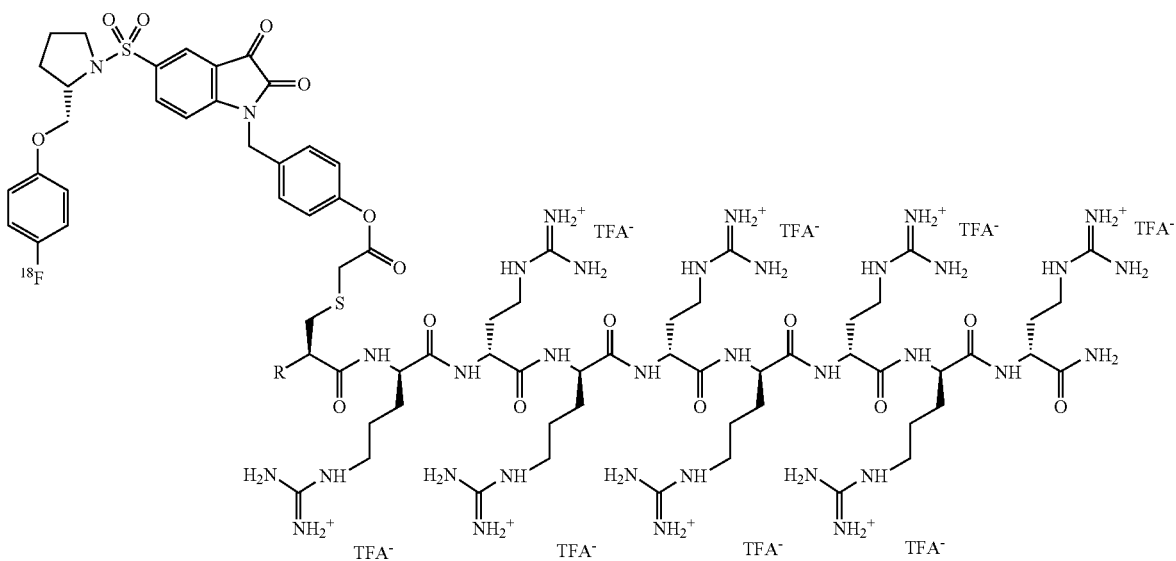

Synthesis of Phosphatidyl Serinopathy-Dependent CbR-AnnexinV Conjugates.

Similarly also a [$^{11}$C], [$^{18}$F]— or [$^{123}$I]-CbR-AnnexinV conjugate is synthesized. Scheme 7 shows the synthesis in accordance with the synthesis of 4-[$^{18}$F]fluorobenzoyl-annexinV ([$^{18}$F]FBA) [37] which is congruent to the above synthesis of the corresponding octaarginine conjugate.

same but analogous PET-compatible conjugate —[$^{18}$F]— or [$^{11}$C]— labeled at the CbR site—can be applied. The result is an image depicting phosphatidyl serinopathy using SPECT (e.g. CbR-[$^{99m}$Tc]Tc-HYNIC-AnnexinV) and depicting intracellular caspase-CbR interaction using PET (e.g. [$^{18}$F]fluoroCbR-AnnexinV). Of course AnnexinV can also be Scheme 7 Synthesis of a [$^{18}$F]-labeled CbR-AnnexinV conjugate

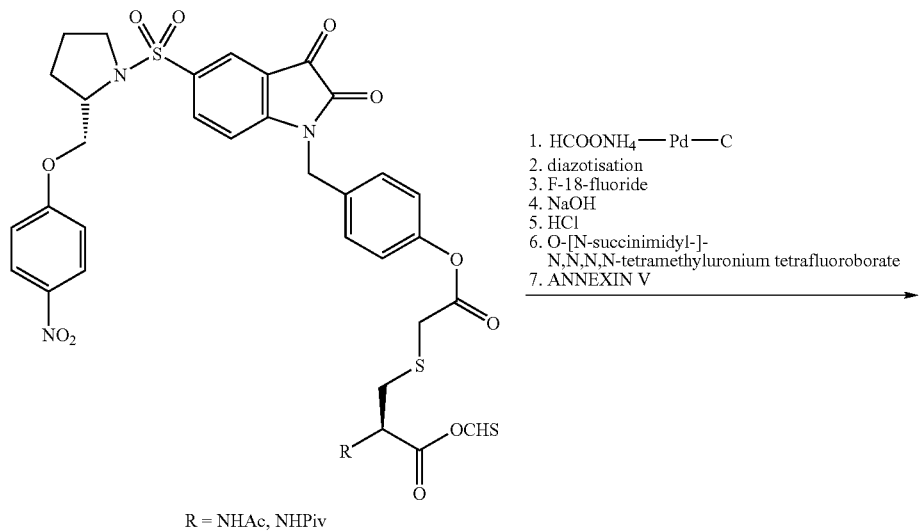

1. HCOONH$_4$ — Pd — C
2. diazotisation
3. F-18-fluoride
4. NaOH
5. HCl
6. O-[N-succinimidyl-]-N,N,N,N-tetramethyluronium tetrafluoroborate
7. ANNEXIN V R = NHAc, NHPiv

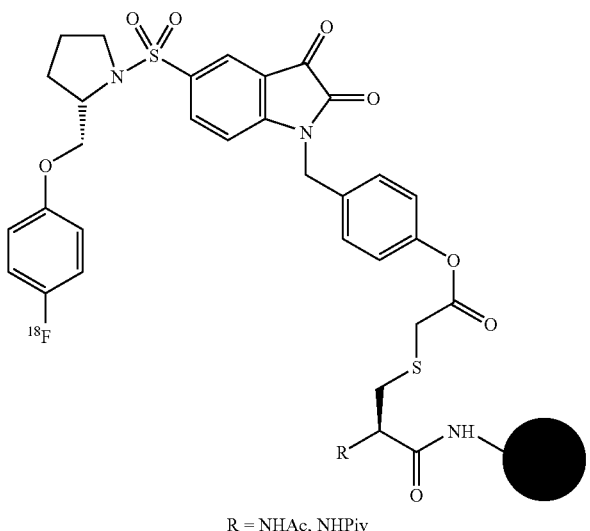

R = NHAc, NHPiv

An accordingly modifiable isatin which can be prepared for radioactive labeling may be radiolabeled via automated synthesis and coupled with the protein AnnexinV.

Synthesis of Dual Specificity Probes for Apoptosis.

Phosphatidyl serinopathy-dependent CbR-AnnexinV conjugates may be labeled with different radioisotopes.

AnnexinV may be first labeled with [$^{99m}$Tc] or [$^{123}$I] and the thus obtained product may be used as a radiosynthon for conjugation with non-radiolabeled CbR. In a double-nuclide study first the SPECT-compatible conjugate —[$^{99m}$Tc]— or [$^{123}$I]— labeled at the Annexin V site—and subsequently the labeled as a PET-compatible phosphatidyl serinopathy CbR-transporter conjugate with a $^{68}$Ga-chelator and subsequently the CbR portion may be labeled with [$^{123}$I] reflecting the Caspase-CbR interaction using SPECT.

This provides a meaningful tool for the detection of individual cell reactions to a potentially deadly stimulus which can be used to differentiate between potentially reversible PS-exposition in myocardial ischemia (determining the area at risk) and apoptotic tissue (moribund by caspases) (see Table 6 for preferable variations).

Synthesis of the Compounds of the Invention

1. Synthesis of 5-Pyrrolidinylsulfonyl Isatins

Scheme 8: General synthesis route for the preparation of [$^{11}$C]I

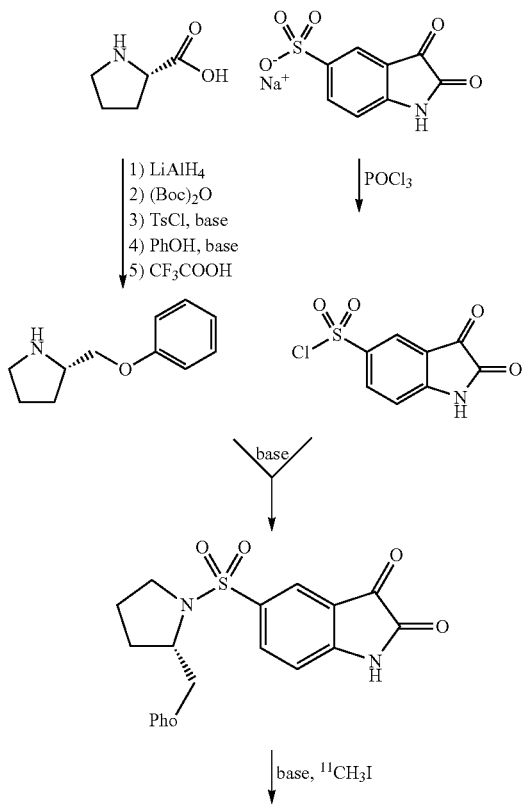

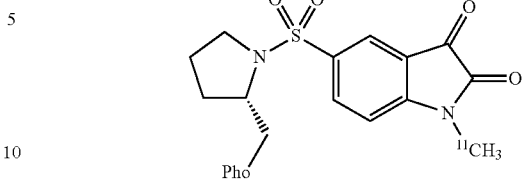

The compounds of structures I and IIa were synthesised according to Lee et al. [20-21]. In scheme 8 the general synthesis route for the preparation of the potential PET-compatible CbR radiotracer (S)-1-[$^{11}$C]methyl-5-(1-[2-(phenoxymethyl)pyrrolidinyl]sulfonyl)isatin [$^{11}$C]I is exemplified.

It will be apparent for the person of ordinary skill in the art how to vary the above scheme 8 to arrive at the other compounds with various $R_1$-X-Y as well as $R_2$ substituents.

A General Procedure for the Synthesis of New Isatin Derivatives is as Follows:

5-[1-(2-phenoxymethylpyrrolidinyl)-sulfonyl]isatin Ia or 5-[1-(2-methoxymethylpyrrolidinyl)sulfonyl]isatin IIa (Scheme 9) were placed in a round bottom flask and dissolved in 50 mL of dry dimethylformamide. Under argon-atmosphere 1 equivalent of sodium hydride was added. During stirring for 30 minutes at room temperature the solution became dark red. Afterwards an access of the benzylbromide was added and the reaction mixture was stirred for another 3 hours at room temperature. In the case of benzylchlorides the reaction mixture was warmed up to 80° C. Removal of the solvent in vacuo afforded the crude product, which was purified by silica gel chromatography.

Scheme 9:

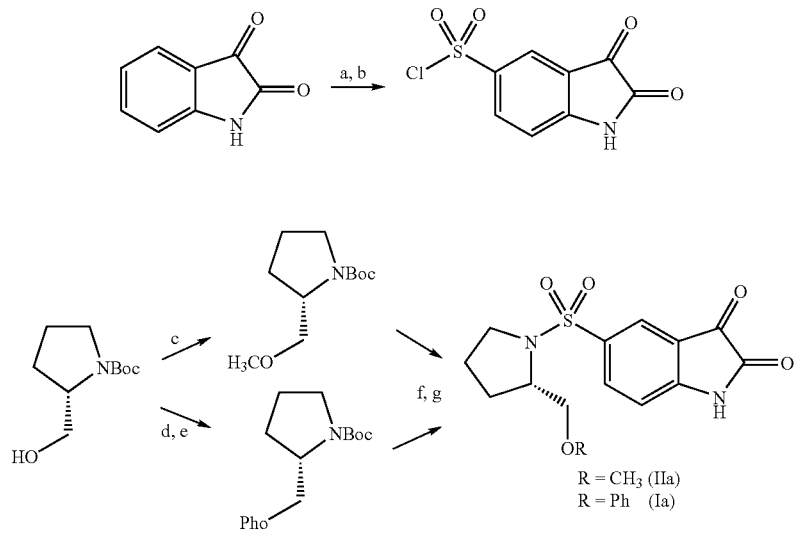

(a) $H_2SO_4/SO_3$; (b) $POCl_3$, tetramethylsulfone; (c) NaH, MeI, THF; (d) TosCl, pyridine, $CH_2Cl_2$; (e) NaH, phenol, THF; (f) TFA, $CH_2Cl_2$; (g) isatin-5-sulfonic acid chloride, Hünigs base, $CHCl_3$/THF.

EXAMPLES

1.1. PET-compatible references (I, II, III, IV, V etc.)

1.1.1 Synthesis of (S)-(+)-1-(methyl)-5-[1-(2-phenoxymethylpyrrolidinyl)sulfonyl]isatin I (Compound I was Synthesised in Accordance to Ref. [21].)

(S)-5-[1-(2-phenoxymethylpyrrolidinyl)sulfonyl]isatin Ia (500 mg, 1.3 mmol) was reacted with sodium hydride (52 mg, 1.3 mmol, 60% in mineral oil) and methyl iodide (553 mg, 3.9 mmol, 0.24 mL) as described in the general procedure and stirred 5 h at room temperature. The crude orange product was purified by silica gel chromatography (diisopropyl ether:acetone 6:1) and yielded I as an orange solid.

Yield: 280 mg (0.7 mmol, 54%). $^1$H-NMR (300 MHz, $d_6$-DMSO): δ [ppm]: 1.58-1.67, 1.83-1.93, 3.20-3.37, 3.39-3.43, 3.89-4.11 (m, 9H, pyrrolidine-CH/$H_2$, $OCH_2$), 3.17 (s, 3H, $NCH_3$), 6.90-6.93 (m, 3H, Ar—H), 7.28 (d, 1H, $^3J_{H,H}$=8.1 Hz, isatin-H), 7.25-7.31 (m, 2H, ArH), 7.81 (d, 1H, $^4J_{H,H}$=1.8 Hz, isatin-H), 8.12 (dd, 1H, $^3J_{H,H}$=8.1 HZ, $^4J_{H,H}$=1.8 Hz, isatin-H). $^{13}$C-NMR (75 MHz, $d_6$-DMSO): δ [ppm]: 24.0, 28.8 (pyrrolidine-$CH_2$), 26.7 ($NCH_3$), 49.6, 58.7 (pyrrolidine-$NCH_2$), 69.9 ($OCH_2$), 111.6, 114.8 (ArCH), 118.1 (q-ArCCO), 121.2, 122.8, 129.9, 131.8 (ArCH), 137.1 (q-Ar$CSO_2$), 154.6 (q-ArCNH), 158.5 (q-ArC), 158.8 (COCONH), 187.5 (COCONH).

MS (EI): m/e (intensity %): 400 ($M^+$, 28), 293 (100), 224 (76), 160 (48).

Anal ($C_{20}H_{20}N_2O_5S$)C, H, N; calcd: C, 59.99; H, 5.03; N, 7.00; found: C, 59.90; H, 4.95; N, 6.99.

1.1.2 Synthesis of (S)-5-[1-(2-methoxymethylpyrrolidinyl)sulfonyl]-1-methyl-isatin II 485 mg (1.25 mmol) of (S)-(+)-5-[1-(2-methoxymethylpyrrolidinyl)sulfonyl]isatin IIa was converted with 50 mg (1 mmol) sodium hydride (60% in mineral oil) and 248 mg (1.5 mmol; 0.1 mL) methyliodide as described in the general procedure and stirred 2 hours at room temperature. The crude dark orange product was purified by silica gel chromatography (diisopropylether/acetone 4:1) and yielded 175 mg of II (0.58 mmol; 46%) as an orange solid.

mp.: 143-144° C.

$^1$H-NMR (300 MHz, $CDCl_3$): δ (ppm)=1.61, 1.82, 3.18, 3.51, 3.52 and 3.68 (bs, 9H, pyrrolidine-$CH_2$ and CH); 3.24 (s, 3H, $OCH_3$); 3.28 (s, 3H, $OCH_3$); 6.94-6.98 (m, 1H, isatin-H); 7.96 (bs, 1H, isatin-H); 8.02-8.04 (m, 1H, isatin-H).

$^{13}$C-NMR (75 MHz, $CDCl_3$): δ (ppm)=26.1, 28.6, 30.8, 32.3, 51.3, 61.0, 61.2, 76.8, 112.2, 119.2, 126.3, 136.0, 139.4, 156.0, 159.8, 183.8.

MS (MALDI-TOF) m/e: 361 ($C_{15}H_{18}N_2O_5S+Na$)$^+$.

Anal. Calc. for $C_{15}H_{18}N_2O_5S$: C, 53.24; H, 5.36; N, 8.28; found: C, 53.54; H, 5.34; N, 8.49.

1.1.3 Synthesis of (S)-1-(4-methoxybenzyl)-5-[1-(2-phenoxymethylpyrrolidinyl)sulfonyl]isatin III 386 mg (1 mmol) of (S)-(+)-5-[1-(2-phenoxymethylpyrrolidinyl)sulfonyl]isatin Ia was converted with 40 mg (1 mmol) sodium hydride (60% in mineral oil) and 670 mg (3 mmol) 4-methoxybenzylchloride as described in the general procedure. The crude dark orange product was purified by silica gel chromatography (diisopropylether/acetone 8:1) and yielded 310 mg of III (0.61 mmol; 61%) as an orange solid.

mp.: 152° C.

$^1$H-NMR (300 MHz, $CDCl_3$): δ (ppm)=1.77-1.81, 2.00-2.04, 3.22-3.26, 3.47-3.51 and 4.15-4.19 (m, 7H, pyrrolidine-$CH_2$ and CH); 3.80 (s, 3H, $OCH_3$); 3.88-3.98 (m, 2H, $PhOCH_2$); 4.86 (s, 2H, $NCH_2Ph$); 6.81-6.98 (m, 6H, PhH, isatin-H); 7.21-7.28 (m, 4H, PhH); 7.95 (dd, 1H, J=1.5 Hz, 8.4 Hz, isatin-H); 8.01 (d, 1H, J=1.8 Hz, isatin-H).

$^{13}$C-NMR (75 MHz, $CDCl_3$): δ (ppm)=26.8, 28.7, 30.0, 43.6, 49.2, 55.0, 58.3, 110.9, 114.0, 114.3, 117.1, 120.7, 123.9, 125.1, 128.4, 128.7, 129.2, 133.8, 136.7, 153.0, 157.4, 157.9, 159.4, 181.4.

MS (EI-directly intake): m/e (intensity %): 506 ($M^+$, 17); 399 (M-$CH_2OPh^+$, 100).

Anal. Calc. for $C_{27}H_{26}N_2O_6S$: C, 64.02; H, 5.17; N, 5.53; found: C, 63.89; H, 5.34; N, 5.51.

1.1.4 Synthesis of (S)-1-(4-methoxybenzyl)-5-[1-(2-methoxymethylpyrrolidinyl)sulfonyl]isatin IV 500 mg (1.54 mmol) of (S)-(+)-5-[1-(2-methoxymethylpyrrolidinyl)sulfonyl]isatin IIa was converted with 61 mg (1.54 mmol) sodium hydride (60% in mineral oil) and 723 mg (0.65 mL, 4.62 mmol) 4-methoxybenzylchloride as described in the general procedure. The crude dark orange product was purified by silica gel chromatography (petrolether/ethyl acetate 3:1-1:1) and yielded 462 mg of IV (1.04 mmol; 68%) as an orange foam.

$^1$H-NMR (300 MHz, $CDCl_3$): δ (ppm)=1.65-1.69, 1.85-1.89, 3.10-3.13, 3.35-3.41 (m, 7H, pyrrolidine-$CH_2$ and CH); 3.33 (s, 3H, $OCH_3$); 3.52-3.54 and 3.72-3.75 (m, 2H, $PhOCH_2$); 3.79 (s, 3H, $PhOCH_3$); 4.90 (s, 2H, $NCH_2Ph$); 6.87 (d, 1H, J=8.1 Hz, isatin-H); 6.94 (d, 2H, J=8.4 Hz, PhH); 7.25 (d, 2H, J=8.4 Hz, PhH); 7.98 (dd, 1H, J=1.8 Hz, 8.1 Hz, isatin-H); 8.02 (d, 1H, J=1.8 Hz, isatin-H).

$^{13}$C-NMR (75 MHz, $CDCl_3$): δ (ppm)=24.1, 28.2, 28.9, 44.0, 49.3, 55.4, 59.1, 74.9, 111.2, 114.6, 117.6, 124.4, 125.8, 129.1, 134.1, 137.3, 153.4, 157.8, 159.8, 181.9.

MS (EI-directly intake): m/e (intensity %): 444 ($M^+$, 90); 399 (M-$CH_2OCH_3^+$, 100).

Anal. Calc. for $C_{22}H_{24}N_2O_6S$: C, 59.45; H, 5.44; N, 6.30; found: C, 59.36; H, 5.46; N, 6.05.

1.1.5 Synthesis of (S)-1-(4-(2-fluoroethoxy)benzyl)-5-[1-(2-phenoxymethylpyrrolidinyl)sulfonyl]isatin V 374 mg (1 mmol) of (S)-(+)-5-[1-(2-phenoxymethylpyrrolidinyl)sulfonyl]isatin Ia was converted with 60 mg (1.5 mmol) sodium hydride (60% in mineral oil) and 1.18 g (5 mmol) 4-(2-fluoroethoxy)benzylbromide as described in the general procedure. The crude dark orange product was purified by silica gel chromatography (cyclohexane/ethyl acetate 1:1) and yielded 170 mg of V (0.32 mmol; 32%) as an orange foam.

mp.: 145-146° C.

$^1$H-NMR (300 MHz, $CDCl_3$): δ (ppm)=1.73-1.84, 1.94-2.06, 3.18-3.26, 3.45-3.51 and 4.13-4.14 (m, 7H, pyrrolidine-$CH_2$ and CH); 3.94-3.97 (m, 2H, $PhOCH_2$); 4.14-4.16, 4.22-4.25, 4.63-4.66, 4.79-4.82 (each m, each 1H, $PhCH_2CH_2F$); 4.85 (s, 2H, $NCH_2Ph$); 6.79-6.92 (m, 6H, PhH and isatin-H); 7.15-7.27 (m, 4H, PhH); 7.93 (dd, 1H, J=1.5 Hz, 8.4 Hz, isatin-H); 7.98 (d, 1H, J=1.5 Hz, isatin-H).

$^{13}$C-NMR (75 MHz, $CDCl_3$): δ (ppm)=24.2, 27.9, 29.1, 43.9, 49.5, 58.7, 67.4, 69.2, 80.7, 82.9, 111.2, 114.4, 115.4, 117.5, 121.1, 124.3, 126.5, 128.2, 129.2, 129.5, 134.2, 137.1, 153.3, 157.8, 158.3, 158.6, 181.8.

$^{19}$F-NMR (282 MHz, $CDCl_3$): δ (ppm)=−224.0.

MS (EI-directly intake): m/e (intensity %): 538 ($M^+$, 8); 431 (M-$CH_2OPh^+$, 100).

Anal. Calc. for $C_{28}H_{27}N_2FO_6S$: C, 62.44; H, 5.05; N, 5.20; found: C, 62.70; H, 5.02; N, 4.91.

1.1.6 Synthesis of (S)-1-(4-(2-fluoroethoxy)benzyl)-5-[1-(2-methoxymethylpyrrolidinyl)sulfonyl]isatin VI 324 mg (1.00 mmol) of (S)-(+)-5-[1-(2-methoxymethylpyrrolidinyl)sulfonyl]isatin IIa was converted with 60 mg (1.5 mmol) sodium hydride (60% in mineral oil) and 1.18 g (5.16 mmol) 4-(2-fluoroethoxy)benzylbromide as described in the general procedure. The crude orange product was purified by silica gel chromatography (petrolether/ethyl acetate 3:1) and yielded 313 mg of VI (0.66 mmol; 66%) as a yellow powder.

mp.: 68-69° C.

$^1$H-NMR (300 MHz, CDCl$_3$): δ (ppm)=1.54-1.64, 1.78-1.84, 3.00-3.07, 3.45-3.61 and 3.60-3.65 (m, 7H, pyrrolidine-CH$_2$ and CH); 3.25 (s, 3H, OCH$_3$); 3.25-3.35 (m, 2H, CH$_3$OCH$_2$); 4.08, 4.17, 4.58, 4.74 (each dd, each 1H, J=5.2 Hz, PhCH$_2$CH$_2$F); 4.83 (s, 2H, NCH$_2$Ph); 6.81-6.87 (m, 3H, PhH and isatin-H); 7.19-7.23 (m, 2H, PhH); 7.89 (dd, 1H, J=1.5 Hz, 8.1 Hz, isatin-H); 7.95 (d, 1H, J=1.5 Hz, isatin-H).

$^{13}$C-NMR (75 MHz, CDCl$_3$): δ (ppm)=24.5, 29.2, 44.3, 49.7, 59.4, 67.8, 75.2, 81.0, 83.3, 111.6, 115.7, 117.9, 124.8, 126.8, 129.5, 134.6, 137.7, 153.7, 158.2, 159.0, 182.3.

$^{19}$F-NMR (282 MHz, CDCl$_3$): δ (ppm)=−224.0.

MS (EI-directly intake): m/e (intensity %): 476 (M$^+$, 8); 431 (M-CH$_2$OCH$_3$$^+$, 100).

Anal. Calc. for $C_{23}H_{25}N_2FO_6S$: C, 57.97; H, 5.27; N, 5.88; found: C, 57.61; H, 5.18; N, 5.51.

1.2 Precursors for PET Chemistry (Ia, IIa, IIIa, IVa, Va etc.)

1.2.1 Synthesis of (S)-(+)-1-(4-benzyloxybenzyl)-5-[1-(2-phenoxymethylpyrrolidinyl)-sulfonyl]isatin IIIaa 500 mg (1.3 mmol) of (S)-(+)-5-[1-(2-phenoxymethylpyrrolidinyl)sulfonyl]isatin Ia was converted with 52 mg (1.3 mmol) sodium hydride (60% in mineral oil) and 605 mg (2.6 mmol) 4-benzyloxybenzylchloride as described in the general procedure. The crude dark orange product was purified by silica gel chromatography (petrolether/ethyl acetate 3:1) and yielded 675 mg of IIaa (1.16 mmol; 89%) as an orange foam.

mp.: 69-70° C.

$^1$H-NMR (300 MHz, CDCl$_3$): δ (ppm)=1.75-1.85, 1.93-2.05, 3.17-3.25, 3.44-3.50 and 3.90-3.97 (m, 7H, pyrrolidine-CH$_2$ and CH); 3.86-3.91 (m, 2H, PhOCH$_2$); 4.83 (s, 2H, NCH$_2$Ph); 5.03 (s, 2H, NCH$_2$Ph); 6.78-6.96 (m, 7H, isatin-H and PhH); 7.18-7.40 (m, 8H, PhH); 7.93 (dd, 1H, J=1.5 Hz, 7.8 Hz, isatin-H); 7.98 (d, 1H, J=1.5 Hz, isatin-H).

$^{13}$C-NMR (75 MHz, CDCl$_3$): δ (ppm)=26.7, 31.6, 46.5, 52.1, 61.2, 71.7, 72.7, 113.7, 116.9, 118.1, 120.0, 123.6, 126.8, 128.5, 130.0, 131.2, 131.7, 132.1, 136.7, 139.2, 139.6, 155.9, 160.3, 161.5, 182.8.

MS (MALDI-TOF) m/e: 606 ($C_{33}H_{30}N_2O_6S$+Na)$^+$.

Anal. Calc. for $C_{33}H_{30}N_2O_6S$: C, 68.03; H, 5.19; N, 4.81; found: C, 68.38; H, 5.34; N, 4.51.

1.2.2 Synthesis of (S)-1-(p-tert-butyldimethylsilyloxybenzyl)-5-[1-(2-phenoxymethylpyrrolidinyl)sulfonyl]-isatin IIIab (S)-5-[1-(2-Phenoxymethylpyrrolidinyl)sulfonyl]isatin Ia (750 mg, 2 mmol) was reacted with sodium hydride (88 mg, 2.2 mmol, 60% in mineral oil) and p-[(tert-butyldimethylsilyl)oxy]benzylbromide (1.81 g, 6 mmol) as described in the general procedure. The crude orange product was purified by silica gel chromatography (cyclohexane:ethyl acetate 9:1 to 4:1) to yield a yellow sticky oil.

Yield: 630 mg (1.01 mmol, 52%).

$^1$H-NMR (400 MHz, CDCl$_3$): δ [ppm]: 0.18 (s, 6H, SiCH$_3$); 0.97 (s, 9H, SitBu); 1.77-1.80, 1.99-2.05, 3.22-3.24, 3.48-3.51, 3.89-3.97, 4.14-4.17 (m, 9H, pyrrolidine-CH/H$_2$, CH$_2$O); 4.84 (s, 2H, NCH$_2$Ar); 6.80-6.94 (m, 6H, Ar—H, isatin-H), 7.17-7.24 (m, 4H, Ar—H); 7.94 (dd, 1H, $^3$J$_{H,H}$=8.4 HZ, $^4$J$_{H,H}$=1.6 Hz, isatin-H); 8.07 (d, 1H, $^4$J$_{H,H}$=1.6 Hz, isatin-H). $^{13}$C-NMR (100 MHz, CDCl$_3$): δ [ppm]: −4.6 (SiCH$_3$), 18.1 (SiCCH$_3$), 26.8 (C(CH$_3$)$_3$), 24.0, 28.9, 49.4, 58.5 (pyrrolidine-C), 43.9 (CCH$_2$Ar), 69.0 (OCH$_2$), 117.0 (q-ArC(CO)), 114.3, 120.2, 122.7, 122.8, 124.1, 126.2, 128.9 (ArC), 129.4 (q-CCH$_2$N), 134.1 (isatin-CH), 136.9 (q-CSO$_2$), 153.3 (q-CN(CO)), 155.9 (q-COSi), 157.6 (isatin-N(CO)), 158.1 (q-COCH$_2$), 181.6 (N(CO)CO).

MS (MALDI-TOF) m/e: 629 (M+Na)$^+$; 607 (M+H)$^+$.

Anal. Calc. for $C_{32}H_{38}N_2O_6SSi$+EtOAc: C, 62.22; H, 6.67; N, 4.03; found: C, 62.01; H, 6.57; N, 4.04.

1.2.3 Synthesis of (S)-(+)-1-(4-benzyloxybenzyl)-5-[1-(2-methoxymethylpyrrolidinyl)-sulfonyl]isatin IVaa 560 mg (1.72 mmol) of (S)-(+)-5-[1-(2-methoxymethylpyrrolidinyl)sulfonyl]isatin IIa was converted with 69 mg (1.72 mmol) sodium hydride (60% in mineral oil) and 1.2 g (5.16 mmol) 4-benzyloxybenzylchloride as described in the general procedure. The crude orange product was purified by silica gel chromatography (petrolether/ethyl acetate 3:1) and yielded 700 mg of IVaa (1.34 mmol; 78%) as a yellow powder.

mp.: 73-74° C.

$^1$H-NMR (300 MHz, CDCl$_3$): δ (ppm)=1.65-1.69, 1.85-1.89, 3.10-3.12, 3.52-3.57 and 3.70-3.73 (m, 7H, pyrrolidine-CH$_2$ and CH); 3.32 (s, 3H, OCH$_3$); 3.34-3.39 (m, 2H, CH$_3$OCH$_2$); 4.89 (s, 2H, NCH$_2$Ph); 5.04 (s, 2H, OCH$_2$Ph); 6.92-6.97 (m, 4H, PhH); 7.25-7.41 (m, 6H, PhH and isatin-H); 7.96 (dd, 1H, J=1.5 Hz, 8.4 Hz, isatin-H); 8.02 (d, 1H, J=1.5 Hz, isatin-H).

$^{13}$C-NMR (75 MHz, CDCl$_3$): δ (ppm)=24.1, 28.7, 44.0, 49.3, 59.1, 70.2, 74.9, 111.3, 115.6, 117.5, 124.4, 126.1, 127.5, 128.1, 128.6, 129.1, 134.1, 136.6, 137.3, 153.4, 157.9, 159.0, 181.9.

MS (EI-directly intake): m/e (intensity %): 520 (M$^+$, 15); 475 (M-CH$_2$OCH$_3$$^+$, 100).

1.2.4 Synthesis of (S)-1-(p-tert-butyldimethylsilyloxybenzyl)-5-[1-(2-methoxymethylpyrrolidinyl)sulfonyl]-isatin IVab (S)-5-[1-(2-Methoxymethylpyrrolidinyl)sulfonyl]isatin IIa (648 mg, 2 mmol) was reacted with sodium hydride (88 mg, 2.2 mmol, 60% in mineral oil) and p-[(tert-butyldimethylsilyl)oxy]benzylbromide (1.81 g, 6 mmol) as described in the general procedure. The crude orange product was purified by silica gel chromatography (cyclohexane:ethyl acetate 9:1 to 3:2) and yielded IVab as a yellow sticky oil.

Yield: 510 mg (0.94 mmol, 47%).

$^1$H-NMR (400 MHz, CDCl$_3$): δ [ppm]: 0.18 (s, 6H, SiCH$_3$); 0.97 (s, 9H, SitBu); 1.65-1.67, 1.88-1.90, 3.09-3.12, 3.40-3.42, 3.54-3.57, 3.71-3.73 (m, 9H, pyrrolidine-CH/H$_2$, CH$_2$O); 3.33 (s, 3H, OCH$_3$); 4.89 (s, 2H, NCH$_2$Ar); 6.83 (d, 2H, $^3$J$_{H,H}$=8.4 Hz, Ar—H), 6.93 (d, 1H, $^3$J$_{H,H}$=8.4 Hz, isatin- H); 7.20 (d, 2H, $^3J_{H,H}$=8.4 Hz, Ar—H); 7.97 (dd, 1H, $^3J_{H,H}$=8.4 Hz, $^4J_{H,H}$=1.6 Hz, isatin-H); 8.04 (d, 1H, $^4J_{H,H}$=1.6 Hz, isatin-H). $^{13}$C-NMR (100 MHz, CDCl$_3$): δ [ppm]: −4.6 (SiCH$_3$), 18.1 (SiCCH$_3$), 25.5 (C(CH$_3$)$_3$), 24.0, 28.7, 49.2, 58.9 (pyrrolidine-C), 43.8 (NCH$_2$Ar), 59.1 (OCH$_3$), 74.7 (OCH$_2$), 117.2 (q-ArC(CO)), 120.2, 122.7, 122.8, 124.3 (Ar—C), 129.5 (q-CCH$_2$N), 134.1 (isatin-CH), 137.1 (q-CSO$_2$), 153.3 (q-CN(CO)), 155.8 (q-COSi), 157.7 (isatin-N(CO)), 181.8 (N(CO)CO).

MS (MALDI-TOF) m/e: 567 (M+Na)$^+$, 545 (M+H)$^+$.

Anal. Calc. for C$_{27}$H$_{36}$N$_2$O$_6$SSi: C, 59.53; H, 6.66; N, 5.14; found: C, 59.87; H, 6.38; N, 4.89.

1.2.5 Synthesis of (S)-1-(p-hydroxybenzyl)-5-[1-(2-phenoxymethylpyrrolidinyl)sulfonyl]isatin IIIa (S)-1-(p-tert-Butyldimethylsilyloxybenzyl)-5-[1-(2-phenoxymethyl-pyrrolidinyl)sulfonyl]isatin IIIab (400 mg, 0.66 mmol) was dissolved in methanol (15 mL) and conc. HCl (1 mL) was added. The resulting mixture was stirred for 2 h at ambient temperature and then diluted with ethyl acetate (100 mL). The organic layer was washed with NaHCO$_3$, water and brine and dried with magnesium sulphate. After removal of the solvent the yellow residue was purified by silica gel chromatography (cyclohexane:ethyl acetate 2:1 to 3:2) to yield a yellow sticky oil.

Yield: 210 mg (0.43 mmol, 65%).

$^1$H-NMR (300 MHz, CDCl$_3$): δ [ppm]: 1.71-1.82, 1.91-2.05, 3.19-3.26, 3.43-3.51, 3.60-3.71, 4.12-4.16 (m, 9H, pyrrolidine-CH/H$_2$, CH$_2$O); 4.82 (s, 2H, NCH$_2$Ar); 5.58 (m, 1H, ArOH); 6.79-6.94 (m, 6H, Ar—H, isatin-H), 7.17-7.31 (m, 4H, Ar—H); 7.95 (dd, 1H, $^3J_{H,H}$=8.4 HZ, $^4J_{H,H}$=1.6 Hz, isatin-H); 7.99 (d, 1H, $^4J_{H,H}$=1.6 Hz, isatin-H). $^{13}$C-NMR (75 MHz, CDCl$_3$): δ [ppm]: 24.5, 29.4, 49.9, 59.1 (pyrrolidine-C), 44.4 (NCH$_2$Ar), 59.2 (OCH$_3$), 72.7 (OCH$_2$), 117.9 (q-ArC(CO)), 116.5, 124.7, 126.1, 127.6, 127.7, 129.1, (Ar—C), 129.6 (q-CCH$_2$N), 134.6 (isatin-CH), 137.5 (q-CSO$_2$), 153.7 (q-CN(CO)), 156.5 (q-COH), 158.2, 158.6 (isatin-N(CO), q-COCH$_2$), 182.2 (N(CO)CO)).

MS (MALDI-TOF) m/e: 516 (M+Na)$^+$, 494 (M+H)$^+$.

Anal. Calc. for C$_{26}$H$_{25}$N$_2$O$_6$S: C, 63.40; H, 4.91; N, 5.69; found: C, 63.25; H, 4.76; N, 5.98.

1.2.6 Synthesis of (S)-1-(p-hydroxybenzyl)-5-[1-(2-methoxymethylpyrrolidinyl)sulfonyl]isatin IVa (S)-1-(p-tert-Butyldimethylsilyloxybenzyl)-5-[1-(2-methoxymethyl-pyrrolidinyl)sulfonyl]isatin IVab (500 mg, 0.92 mmol) was dissolved in methanol (15 mL) and conc. HCl (1 mL) was added. The resulting mixture was stirred for 2 h at ambient temperature and then diluted with ethyl acetate (100 mL). The organic layer was washed with NaHCO$_3$, water and brine and dried with magnesium sulphate. After removal of the solvent the residue was purified by silica gel chromatography (cyclohexane:ethyl acetate 3:2 to 1:1) to yield a yellow sticky oil.

Yield: 350 mg (0.81 mmol, 88%).

$^1$H-NMR (300 MHz, CDCl$_3$): δ [ppm]: 1.65-1.71, 1.85-1.92, 3.10-3.13, 3.41-3.44, 3.53-3.57, 3.71-3.73 (m, 9H, pyrrolidine-CH/H$_2$, CH$_2$O); 3.33 (s, 3H, OCH$_3$); 4.61 (m, 1H, ArOH), 4.87 (s, 2H, NCH$_2$Ar); 6.83 (d, 2H, $^3J_{H,H}$=8.4 HZ, Ar—H), 6.94 (d, 1H, $^3J_{H,H}$=8.4 Hz, isatin-H); 7.18 (d, 2H, $^3J_{H,H}$=8.4 Hz, Ar—H); 7.96 (dd, 1H, $^3J_{H,H}$=8.4 HZ, $^4J_{H,H}$=1.8 Hz, isatin-H); 8.02 (d, 1H, $^4J_{H,H}$=1.8 Hz, isatin-H). $^{13}$C-NMR (75 MHz, CDCl$_3$): δ [ppm]: 24.1, 28.8, 49.3, 59.1 (pyrrolidine-C), 44.1 (CCH$_2$), 59.2 (OCH$_3$), 74.8 (OCH$_2$), 117.5 (q-ArC(CO)), 116.2, 122.8, 124.4, 124.9 (ArC), 129.5 (q-CCH$_2$N), 134.1 (isatin-CH), 137.3 (q-CSO$_2$), 153.5 (q-CN(CO)), 156.9 (q-COH), 157.9 (isatin-N(CO)), 182.0 (N(CO)CO)).

MS (MALDI-TOF) m/e: 453 (M+Na)$^+$, 431 (M+H)$^+$.

Anal. Calc. for C$_{21}$H$_{22}$N$_2$O$_6$S: C, 58.59; H, 5.15; N, 6.51; found: C, 58.72; H, 4.98; N, 6.21.

1.2.7 Synthesis of (S)-1-(4-(2-bromoethoxy)benzyl)-5-[1-(2-phenoxymethylpyrrolidinyl)sulfonyl]isatin Vaa 730 mg (1.90 mmol) of (S)-(+)-5-[1-(2-phenoxymethylpyrrolidinyl)sulfonyl]isatin Ia was converted with 80 mg (1.90 mmol) sodium hydride (60% in mineral oil) and 882 mg (3 mmol) 4-(2-bromoethoxy)benzylbromide as described in the general procedure. The crude orange product was purified by silica gel chromatography (petrolether/ethyl acetate 3:1→1:1) and yielded 910 mg of Vaa (1.52 mmol; 80%) as a yellow solid.

mp.: 162-163° C.

$^1$H-NMR (300 MHz, CDCl$_3$): δ (ppm)=1.68-1.75, 1.91-1.97, 3.13-3.17, 3.39-3.42 (m, 6H, pyrrolidine-CH$_2$ and CH); 3.54 (t, 2H, J=6.0 Hz, PhCH$_2$CH$_2$Br); 3.80-3.90 (m, 2H, PhOCH$_2$); 4.05-4.09 (m, 1H, pyrrolidine-CH); 4.19 (t, 2H, J=6.0 Hz, PhCH$_2$CH$_2$Br); 4.77 (s, 2H, NCH$_2$Ph); 6.71-6.87 (m, 6H, PhH and isatin-H); 7.11-7.20 (m, 4H, PhH); 7.86 (dd, 1H, J=1.8 Hz, 8.4 Hz, isatin-H); 7.91 (d, 1H, J=1.5 Hz, isatin-H).

$^{13}$C-NMR (75 MHz, CDCl$_3$): δ (ppm)=24.5, 29.3, 29.4, 44.3, 49.9, 59.1, 68.4, 69.6, 11.6, 114.8, 115.8, 117.9, 121.5, 124.7, 127.0, 129.6, 129.9, 134.6, 137.5, 153.7, 158.2, 158.6, 182.1.

MS (EI-directly intake): m/e (intensity %): 600 (3), 598 (M$^+$, 3); 493 (100), 491 (M-CH$_2$OPh$^+$, 100).

Anal. Calc. for C$_{28}$H$_{27}$BrN$_2$O$_6$S: C, 56.10; H, 4.54; N, 4.67; found: C, 56.10; H, 4.40; N, 4.56.

1.2.8 Synthesis of (S)-1-(4-(2-(p-methylphenylsulfonyloxy)ethoxy)benzyl)-5-[1-(2-phenoxymethylpyrrolidinyl)sulfonyl]isatin Va 500 mg (0.83 mmol) of (S)-(+)-1-(4-(2-bromoethoxy)benzyl)-5-[1-(2-phenoxymethyl-pyrrolidinyl)sulfonyl]isatin Vaa was solved in 20 mL dry acetonitrile under argon atmosphere. After adding 1.26 g (4 mmol) silver tosylate the reaction mixture was heated to reflux for 24 h. During the reaction grey precipitation was formed. The solvent was removed in vacuo and the crude orange product was purified by silica gel chromatography (toluene/ethyl acetate 2:1). It yielded 510 mg of Va (0.75 mmol; 90%) as an orange solid.

mp.: 83-83° C.

$^1$H-NMR (300 MHz, CDCl$_3$): δ (ppm)=1.74-1.85, 1.95-2.05, 3.22-3.27, 3.46-3.53 (m, 6H, pyrrolidine-CH$_2$ and CH); 2.45 (s, 3H, PhCH$_3$); 3.96-3.99 (m, 2H, PhOCH$_2$); 4.12-4.18 (m, 3H, PhCH$_2$CH$_2$OTos and pyrrolidine-CH); 4.34-4.37 (m, 2H, PhCH$_2$C$_2$HOTos); 4.85 (s, 2H, NCH$_2$Ph); 6.79-6.94 (m, 6H, PhH and isatin-H); 7.21-7.36 (m, 6H, PhH); 7.79-7.82 (m, 2H, PhH); 7.96 (dd, 1H, J=1.8 Hz, 8.4 Hz, isatin-H); 8.00 (d, 1H, J=1.8 Hz, isatin-H).

$^{13}$C-NMR (75 MHz, CDCl$_3$): δ (ppm)=22.0, 24.5, 29.4, 44.3, 49.9, 59.1, 66.1, 68.3, 69.6, 111.6, 114.8, 115.7, 117.9, 121.4, 124.6, 126.9, 128.4, 128.6, 129.5, 129.9, 130.3, 133.3, 134.6, 137.5, 145.4, 153.7, 158.2, 158.6, 182.1.

MS (EI-directly intake): m/e (intensity %): 583 (M-PhOCH$_2^+$, 10); 385 (Ia$^+$, 39); 91 (100) (PhCH$_2^+$, 100)

Anal. Calc. for $C_{35}H_{34}N_2O_9S_2$: C, 60.85; H, 4.96; N, 4.06; found: C, 61.04; H, 4.87; N, 3.88.

1.2.9 Synthesis of (S)-1-(4-(2-bromoethoxy)benzyl)-5-[1-(2-methoxymethylpyrrolidinyl)-sulfonyl]isatin VIaa 800 mg (2.46 mmol) of (S)-(+)-5-[1-(2-methoxymethylpyrrolidinyl)sulfonyl]isatin IIa was converted with 98 mg (2.46 mmol) sodium hydride (60% in mineral oil) and 1.4 g (4.92 mmol) 4-(2-bromoethoxy)benzylbromide as described in the general procedure. The crude orange product was purified by silica gel chromatography (petrolether/ethyl acetate 3:141:2) and yielded 1.02 g of VIaa (1.90 mmol; 77%) as a yellow foam.

mp.: 61-62° C.

$^1$H-NMR (300 MHz, CDCl$_3$): δ (ppm)=1.66-1.70, 1.86-1.90, 3.10-3.13, 3.53-3.57 and 3.71-3.73 (m, 7H, pyrrolidine-CH$_2$ and CH); 3.33 (s, 3H, OCH$_3$); 3.35-3.39 (m, 2H, CH$_3$OCH$_2$); 3.63 (t, 2H, J=5.7 Hz, PhCH$_2$CH$_2$Br); 4.28 (t, 2H, J=5.7 Hz, PhCH$_2$CH$_2$Br); 4.91 (s, 2H, NCH$_2$Ph); 6.89-6.97 (m, 3H, PhH and isatin-H); 7.27-7.30 (m, 2H, PhH); 7.97 (dd, 1H, J=1.8 Hz, 8.4 Hz, isatin-H); 8.02 (d, 1H, J=1.5 Hz, isatin-H).

$^{13}$C-NMR (75 MHz, CDCl$_3$): δ (ppm)=24.5, 29.2, 29.4, 44.3, 49.7, 59.4, 68.4, 75.2, 111.6, 115.8, 117.9, 124.8, 127.0, 129.6, 134.7, 137.7, 153.7, 158.2, 158.6, 182.3.

MS (EI-directly intake): m/e (intensity %): 538 (42), 536 (42) (M$^+$, 42); 493 (100), 491 (100) (M-CH$_2$OCH$_3$$^+$, 100).

Anal. Calc. for $C_{23}H_{25}BrN_2O_6S$: C, 51.40; H, 4.69; N, 5.21; found: C, 51.08; H, 4.48; N, 5.00.

1.2.10 Synthesis of (S)-1-(4-(2-(p-methylphenylsulfonyloxy)ethoxy)benzyl)-5-[1-(2-methoxymethylpyrrolidinyl)sulfonyl]isatin VIa 500 mg (0.93 mmol) of (S)-(+)-1-(4-(2-bromoethoxy)benzyl)-5-[1-(2-methoxymethyl-pyrrolidinyl)sulfonyl]isatin VIaa was solved in 20 mL dry acetonitrile under argon atmosphere. After adding 1.26 g (4 mmol) silver tosylate the reaction mixture was heated to reflux for 24 h. During the reaction grey precipitation was formed. The solvent was removed in vacuo and the crude orange product was purified by silica gel chromatography (toluene/ethyl acetate 2:1). It yielded 540 mg of VIa (0.88 mmol; 94%) as an orange solid.

mp.: 61-62° C.

$^1$H-NMR (300 MHz, CDCl$_3$): δ (ppm)=1.63-1.68, 1.85-1.89, 3.09-3.13, 3.52-3.57 and 3.70-3.74 (m, 7H, pyrrolidine-CH$_2$ and CH); 2.44 (s, 3H, PhCH$_3$); 3.33 (s, 3H, OCH$_3$); 3.33-3.39 (m, 2H, CH$_3$OCH$_2$); 4.12-4.15 (m, 2H, PhCH$_2$CH$_2$OTos); 4.33-4.36 (m, 2H, PhCH$_2$C$_2$HOTos); 4.89 (s, 2H, NCH$_2$Ph); 6.78-6.81 (m, 2H, PhH) 6.91 (d, 1H, J=8.4 Hz, isatin-H); 7.15-7.35 (m, 6H, PhH); 7.78-7.82 (m, 2H, PhH), 7.97 (dd, 1H, J=1.8 Hz, 8.4 Hz, isatin-H); 8.03 (d, 1H, J=1.8 Hz, isatin-H).

$^{13}$C-NMR (75 MHz, CDCl$_3$): δ (ppm)=22.0, 24.5, 29.2, 44.3, 49.7, 59.6, 60.7, 66.0, 68.3, 75.2, 111.5, 115.7, 117.9, 124.8, 126.9, 128.4, 129.4, 130.3, 133.3, 134.7, 137.7, 145.4, 153.7, 158.2, 158.6, 182.3.

MS (EI-directly intake): m/e (intensity %): 628 (M$^+$, 1.5); 583(100) (M-CH$_2$OCH$_3$$^+$, 100).

Anal. Calc. for $C_{30}H_{32}N_2O_9S_2$: C, 57.31; H, 5.13; N, 4.36; found: C, 57.36; H, 5.25; N, 3.99.

1.3 SPECT-compatible references (1, 2, 3, 4, 5 etc.)

1.3.1 Synthesis of (S)-1-(4-iodobenzyl)-5-[1-(2-phenoxymethylpyrrolidinyl)sulfonyl]isatin 1

385 mg (1 mmol) of (S)-(+)-5-[1-(2-phenoxymethylpyrrolidinyl)sulfonyl]isatin Ia was converted with 40 mg (1 mmol) sodium hydride (60% in mineral oil) and 445 mg (1.5 mmol) 4-iodobenzylbromide as described in the general procedure. The crude dark orange product was purified by silica gel chromatography (diisopropylether/acetone 4:1) and yielded 400 mg of 1 (0.66 mmol; 66%) as an orange solid.

mp.: 88-90° C.

$^1$H-NMR (300 MHz, CDCl$_3$): δ (ppm)=1.71-1.74, 1.91-1.98, 3.13-3.18, 3.39-3.43 and 4.05-4.09 (m, 7H, pyrrolidine-CH$_2$ and CH); 3.81-3.91 (m, 2H, PhOCH$_2$); 4.78 (s, 2H, NCH$_2$Ph); 6.72-6.76 (m, 3H, isatin-H and PhH); 6.83-6.87 (m, 1H, PhH); 6.98-7.01 (m, 2H, PhH); 7.13-7.19 (m, 2H, PhH); 7.61-7.63 (m, 2H, PhH); 7.86 (dd, 1H, J=1.5 Hz, 7.8 Hz, isatin-H); 7.93 (d, 1H, J=1.5 Hz, isatin-H).

$^{13}$C-NMR (100 MHz, CDCl$_3$): δ (ppm)=24.1, 28.9, 43.8, 49.4, 58.6, 69.1, 94.0, 110.9, 114.3, 117.4, 120.9, 124.3, 129.2, 129.3, 129.4, 133.4, 134.4, 137.0, 138.3, 152.8, 157.7, 158.1, 181.3.

MS (ES): m/e (intensity %): 657 (100) (M+MeOH+Na)$^+$; 625 (25) (M+Na)$^+$; 603 (10) (M+H)$^+$.

Anal. Calc. for $C_{26}H_{23}IN_2O_5S$: C, 51.84; H, 3.85; N, 4.65; found: 52.29; H, 4.11; N, 4.57.

1.3.2 Synthesis of (S)-1-(4-iodobenzyl)-5-[1-(2-methoxymethylpyrrolidinyl)sulfonyl]isatin 2

750 mg (2.3 mmol) of (S)-(+)-5-[1-(2-methoxymethylpyrrolidinyl)sulfonyl]isatin IIa was converted with 92 mg (2.3 mmol) sodium hydride (60% in mineral oil) and 1.02 g (3.45 mmol) 4-iodobenzylbromide as described in the general procedure. The crude dark orange product was purified by silica gel chromatography (diisopropyl ether/acetone 8:1) and yielded 820 mg of 2 (1.52 mmol; 66%) as an orange solid.

mp.: 129-130° C.

$^1$H-NMR (300 MHz, CDCl$_3$): δ (ppm)=1.64-1.69, 1.86-1.91, 3.11-3.13, 3.35-3.41 (m, 7H, pyrrolidine-CH$_2$ and CH); 3.30 (s, 3H, OCH$_3$); 3.52-3.57 and 3.72-3.74 (m, 2H, PhOCH$_2$); 4.91 (s, 2H, NCH$_2$Ph); 6.87 (d, 1H, J=8.4 Hz, isatin-H); 7.08 (d, 2H, J=8.7 Hz, PhH); 7.69 (d, 2H, J=8.7 Hz, PhH); 7.97 (dd, 1H, J=1.8 Hz, 8.4 Hz, isatin-H); 8.04 (d, 1H, J=1.8 Hz, isatin-H).

$^{13}$C-NMR (75 MHz, CDCl$_3$): δ (ppm)=24.1, 27.2, 28.9, 44.0, 49.2, 59.1, 59.2, 74.8, 94.1, 111.0, 117.6, 124.6, 129.4, 133.5, 134.5, 137.4, 138.4, 153.0, 157.8, 181.5.

MS (EI-directly intake): m/e (intensity %): 540 (M$^+$, 2); 495 (100) (M-CH$_2$OCH$_3$$^+$, 100).

Anal. Calc. for $C_{21}H_{21}N_2IO_5S$: C, 46.68; H, 3.92; N, 5.18; found: 47.00; H, 3.91; N, 5.01.

1.4 Precursors for SPECT Chemistry (1a, 2a, 3a, 5a etc.)

1.4.1 Synthesis of (S)-5-[1-(2-phenoxymethylpyrrolidinyl)sulfonyl]-1-(4-tributylstannylbenzyl)-isatin 1a 385 mg (1 mmol) of (S)-(+)-5-[1-(2-phenoxymethylpyrrolidinyl)sulfonyl]isatin Ia was converted with 60 mg (1.5 mmol) sodium hydride (60% in mineral oil) and 1.42 g (3 mmol) 4-Tributylstannylbenzylmethansulfonate as described in the general procedure. The crude orange product was purified by silica gel chromatography (petrolether/ethyl acetate 6:1) and yielded 410 mg of 1 (0.53 mmol; 53%) as an orange oil.

$^1$H-NMR (300 MHz, CDCl$_3$): δ (ppm)=0.92 (t, 12H, J=7.5 Hz, SnBu-CH$_3$); 1.07-1.13, 1.31-1.43, 1.53-1.60 (m, 18H, SnCH$_2$) 1.81-1.89, 2.04-2.11, 3.28-3.34, 3.50-3.56 (m, 7H, pyrrolidine-CH$_2$ and CH); 3.94-4.04 and 4.19-4.23 (m, 2H, PhOCH$_2$); 4.94 (s, 2H, NCH$_2$Ph); 6.86 (d, 2H, J=8.1 Hz, 4-SnBu$_3$PhH); 6.91-6.99 (m, 2H, PhH); 7.23-7.34 (m, 4H, PhH); 7.51 (d, 2H, J=8.1 Hz, 4-SnBu$_3$PhH); 8.00 (dd, 1H, J=1.8 Hz, 8.4 Hz, isatin-H); 8.07 (d, 1H, J=1.8 Hz, isatin-H).

$^{13}$C-NMR (75 MHz, CDCl$_3$): δ (ppm)=10.0, 14.0, 24.6, 27.7, 28.2, 29.4, 44.8, 49.9, 59.1, 69.6, 111.6, 114.8, 117.9, 121.5, 124.6, 127.4, 129.9, 133.7, 134.7, 137.5, 143.4, 153.8, 158.2, 158.6, 180.1, 182.1.

MS (MALDI-TOF) m/e: 709 (C$_{38}$H$_{50}$N$_2$O$_5$SSn—C$_4$H$_9$)$^+$.

1.4.2 Synthesis of (S)-5-[1-(2-phenoxymethylpyrrolidinyl)sulfonyl]-1-(4-trimethylsilylbenzyl)-isatin 1b 500 mg (1.29 mmol) of (S)-(+)-5-[1-(2-phenoxymethylpyrrolidinyl)sulfonyl]isatin Ia was converted with 64 mg (1.61 mmol) sodium hydride (60% in mineral oil) and 314 mg (1.29 mmol) 4-trimethylsilylbenzylbromide as described in the general procedure and stirred 21 hours at room temperature. The reaction mixture was diluted with 50 mL water and extracted with 100 mL chloroform three times. The combined organic extracts were washed with brine and dried (Na$_2$SO$_4$). After evaporation the product was purified by silica gel chromatography (petrolether/ethyl acetate 2:1) and yielded 217 mg of 1b (0.4 mmol; 31%) as an orange solid.

mp.: 128-130° C. (decomposition)

$^1$H-NMR (300 MHz, CDCl$_3$): δ (ppm)=0.25 (s, 9H, Si(CH$_3$)$_3$); 1.77-1.81, 1.99-2.05, 3.23-3.26, 3.47-3.49 and 3.88-4.17 (m, 9H, pyrrolidine-CH$_2$ and CH); 4.90 (s, 2H, NCH$_2$Ph); 6.79-6.94 (m, 4H, isatin-H and PhH); 7.19-7.30 (m, 4H, PhH); 7.50-7.53 (m, 2H, PhH); 7.95 (dd, 1H, J=1.8 Hz, 8.4 Hz, isatin-H); 8.01 (d, 1H, J=1.8 Hz, isatin-H).

$^{13}$C-NMR (75 MHz, CDCl$_3$): δ (ppm)=−1.21, 14.2, 24.2, 29.1, 44.4, 49.5, 58.7, 69.2, 111.2, 114.4, 117.5, 121.1, 124.3, 126.9, 129.5, 134.2, 137.1, 141.3, 153.7, 158.0, 158.3, 182.2.

MS (EI-directly intake): m/e (intensity %): 548 (M$^+$, 5); 441 (M-CH$_2$OPh$^+$, 100).

Anal. Calc. for C$_{29}$H$_{32}$N$_2$O$_5$SSi: C, 63.48; H, 5.88; N, 5.11; found: C, 62.67; H, 6.02; N, 4.86.

1.4.3 Synthesis of (S)-(+)-1-(4-bromobenzyl)-5-[1-(2-phenoxymethylpyrrolidinyl)sulfonyl]isatin 1c 500 mg (1.3 mmol) of (S)-(+)-5-[1-(2-phenoxymethylpyrrolidinyl)sulfonyl]isatin Ia was converted with 60 mg (1.5 mmol) sodium hydride (60% in mineral oil) and 647 mg (2.6 mmol) 4-bromobenzylbromide as described in the general procedure. The crude dark orange product was purified by silica gel chromatography (petrolether/ethyl acetate 2:1) and yielded 480 mg of 1c (0.87 mmol; 67%) as an orange solid.

mp.: 74-76° C.

$^1$H-NMR (400 MHz, CDCl$_3$): δ (ppm)=1.78-1.85, 1.98-2.05, 3.23-3.27, 3.47-3.52 and 3.97-3.99 (m, 7H, pyrrolidine-CH$_2$ and CH); 3.89-3.93 (m, 2H, PhOCH$_2$); 4.87 (s, 2H, NCH$_2$Ph); 6.79-6.81 (m, 3H, isatin-H and PhH); 6.91-6.95 (m, 1H, PhH); 7.19-7.26 (m, 4H, PhH); 7.50-7.51 (m, 2H, PhH); 7.96 (dd, 1H, J=1.6 Hz, 8.4 Hz, isatin-H); 8.02 (d, 1H, J=1.6 Hz, isatin-H).

$^{13}$C-NMR (100 MHz, CDCl$_3$): δ (ppm)=24.2, 29.1, 43.9, 49.5, 58.7, 69.1, 75.7, 111.0, 114.4, 117.5, 121.0, 122.7, 124.5, 129.3, 129.5, 132.5, 132.8, 134.7, 137.2, 152.9, 157.8, 158.2, 181.2.

MS (EI-directly intake): m/e (intensity %): 555 (5), 553 (M$^+$, 5); 449 (100), 447 (M-CH$_2$OPh$^+$, 95).

Anal. Calc. for C$_{26}$H$_{23}$BrN$_2$O$_5$S: C, 56.18; H, 4.17; N, 5.04; found: C, 56.50; H, 4.28; N, 4.68.

1.4.4 Synthesis of (S)-5-[1-(2-methoxymethylpyrrolidinyl)sulfonyl]-1-(4-tributylstannylbenzyl)isatin 2a 324 mg (1 mmol) of (S)-(+)-5-[1-(2-methoxymethylpyrrolidinyl)sulfonyl]isatin IIa was converted with 60 mg (1.5 mmol) sodium hydride (60% in mineral oil) and 680 mg (1.4 mmol) 4-tributylstannylbenzylmethansulfonate as described in the general procedure. The crude orange product was purified by silica gel chromatography (petrolether/ethyl acetate 4:1) and yielded 378 mg of 2a (0.54 mmol; 54%) as an orange oil.

$^1$H-NMR (300 MHz, CDCl$_3$): δ (ppm)=0.80 (t, 12H, J=7.5 Hz, SnBu-CH$_3$); 0.94-1.00, 1.16-1.28, 1.39-1.48 (m, 18H, SnCH$_2$) 1.58-1.61, 1.78-1.83, 3.02-3.09, 3.45-3.50, 3.64-3.69 (m, 7H, pyrrolidine-CH$_2$ and CH); 3.25 (s, 3H, CH$_3$OCH$_2$); 3.27-3.35 (m, 2H, CH$_3$OCH$_2$); 4.87 (s, 2H, NCH$_2$Ph); 6.86 (d, 2H, J=8.4 Hz, isatin-H); 7.20 (d, 2H, J=7.2 Hz, 4-SnBu$_3$PhH); 7.38 (d, 2H, J=7.2 Hz, 4-SnBu$_3$PhH); 7.91 (dd, 1H, J=1.8 Hz, 8.4 Hz, isatin-H); 7.97 (d, 1H, J=1.8 Hz, isatin-H).

$^{13}$C-NMR (75 MHz, CDCl$_3$): δ (ppm)=9.6, 13.6, 24.1, 27.3, 28.8, 29.0, 44.4, 49.3, 59.2, 60.3, 74.8, 111.2, 117.5, 124.4, 126.9, 133.2, 137.3, 143.0, 153.4, 157.8, 180.0.

MS (MALDI-TOF) m/e: 647 (C$_{33}$H$_{48}$N$_2$O$_5$SSn—C$_4$H$_9$)$^+$.

Scheme 10: Intermediates for N-1-alkylation of compounds Ia and IIa.

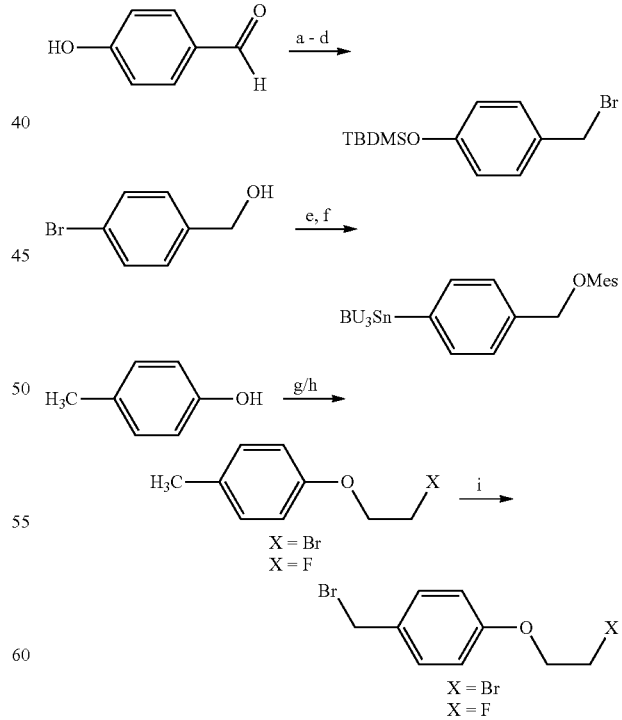

(a) TBDMSCl, imidazole, THF; (b) LiAlH$_4$, THF; (c) TFAA, THF;
(d) LiBr, THF; (e) BuLi, Bu$_3$SnCl, THF; (f) MesCl, NEt$_3$, CH$_2$Cl$_2$;
(g) (X = Br) dibromo ethane, phase transfer catalyst, NaOH, water;
(h) (X = F) fluoroethyl tosylate, Cs$_2$CO$_3$, DMF; (i) NBS, AIBN, CCl$_4$.

Scheme 11: Selection of nonradioactive 5-pyrrolidinylsulfonyl isatins of the present invention
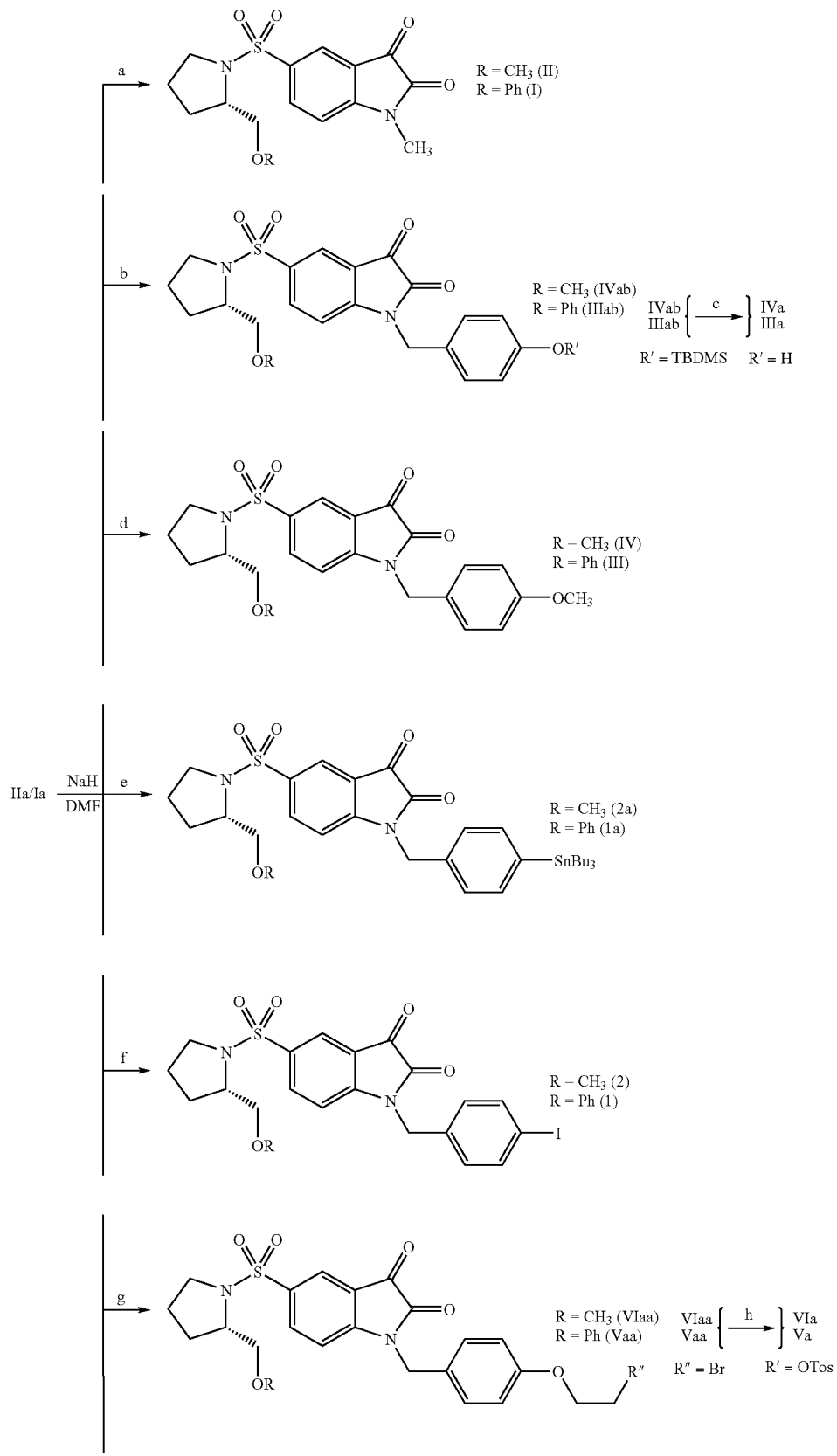

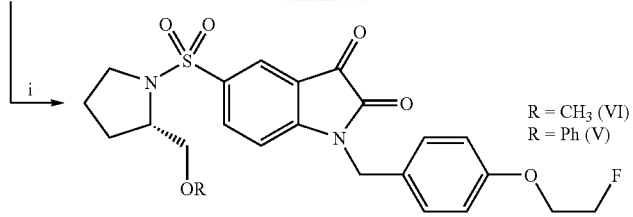

(a) MeI; (b) p-[(tert-butyldimethylsilyl)oxy]benzyl trifluoroacetate; (c) HCl, MeOH; (d) p-methoxy benzylbromide; (e) p-tributylstannylbenzyl methanesulfonate; (f) p-iodo benzylbromide; (g) p-(2-bromoethoxy)bromomethylbenzene; (h) silver p-toluenesulphonate, $CH_3CN$; (i) p-(2-fluoroethoxy)bromomethylbenzene.

2 Radiosynthesis of PET- and SPECT-Compatible CbRs

2.1 PET-compatible CbRs (eg. $[^{11}C]II$, $[^{11}C]III$, $[^{11}C]IV$, $[^{18}F]V$ etc.)

2.1.1 Radiosynthesis[a] of (S)-(+)-1-([$^{11}C$]methyl)-5-[1-(2-phenoxymethylpyrrolidinyl)sulfonyl]isatin $[^{11}C]I$ $[^{11}C]CO_2$ was produced by the $^{14}N(p, \alpha)^{11}C$ nuclear reaction of research grade nitrogen gas target mixture containing 2.5% oxygen with a CTI-RDS-111 cyclotron using 11 MeV proton beams at currents of 40 µA and trapped in a stainless steel loop cooled with liquid nitrogen to −150° C. $[^{11}C]CH_3I$ was prepared from $[^{11}C]CO_2$, 50 µl 1 M $LiAlH_4$ (ABX advanced biochemical compounds), 100 µl 0.5 M $H_3PO_4$, a column filled with $PPh_3I_2$ adsorbed at $Al_2O_3$ (180° C.) and a column filled with $P_2O_5$ using a procedure similar to that previously described [38]. 1.0 mg (2.6 µmol) desmethyl-precursor Ia and 0.2 mg (60% mineral oil, 5.0 µmol) NaH in 200 µl DMF was reacted with $[^{11}C]CH_3I$ at 80° C. for 5 min. After cooling to 50° C., 200 µl water for injection were added and the crude mixture was loaded onto a semi-preparative HPLC-column and the product $[^{11}C]I$ was eluated with $H_2O/CH_3CN$ 65/35 at a flow of 4 ml/min at 43.6-50 min in 150 ml water for injection. The mixture was passed through a C18 SepPake®-cartridge (Waters). The cartridge was washed with 5 ml water for injection and $[^{11}C]I$ was eluated with 2 ml EtOH in 10 mL saline. Finally the solution was filtered through a sterile filter (0.2 µm). The time of synthesis and purification was 91 min from the EOB. The absolute radiochemical yield was 290 MBq. The radiochemical purity, determined via radio-HPLC (eluent: 500 mM $NH_4COO/CH_3CN$ 6/4, flow: 0.3 ml/min, retention time: 23.8 min), was >99% with a specific activity of 1.0 GBq/µmol at the EOS (n=1). Chemical identity of $[^{11}C]I$ was proved by HPLC coinjection of $[^{11}C]I$ and non-radioactive reference I.

[a]Radiosynthesis was carried out using an automated PET Tracer Synthesizer TRACERLab Fxc (GE Functional Imaging GmbH). Separation of the radiosynthesized compounds, and analyses of the radiochemical yields were performed by radio-HPLC using a Syknm S1021 pump, a Knauer K-2001 UV-detector (wavelength 254 nm), a Raytest Ramona-90/92 γ-detector, a Nucleosil 100-10 C18 precolumn (20×8 $mm^2$) and a Nucleosil 100-7 C18 column (250×16 $mm^2$). Sample injection was carried out using a VICI injector block (type C6W incl. 1000 µl loop). The recorded data were processed by the TRACERLab C software (GE Functional Imaging GmbH).

The radiochemical purities and the specific activities were acquired with a radio-HPLC system composed of a Syknm S1021 pump, a Knauer K-2501 UV-detector (wavelength 254 nm), a Crismatec Na(Tl) Scintibloc 51 SP51 γ-detector, a Nucleosil 100-3 C18 column (200×3 $mm^2$), a VICI injector block (type C1 incl. 20 µl loop) and the NINA version 4.8, Rev. 4 software (GE Functional Imaging GmbH).

2.1.2 Radiosynthesis[b] of (S)-1-(4-(2-[$^{18}F$]Fluoroethoxy)benzyl)-5-[1-(2-methoxymethylpyrrolidinyl)-sulfonyl]isatin $[^{18}F]VI$ No-carrier-added aqueous $[^{18}F]$fluoride was produced on a CTI-RDS-111 cyclotron by irradiation of a 1.2 ml water target using 10 MeV proton beams on 97.0% enriched $[^{18}O]$ water by the $^{18}O(p,n)^{18}F$ nuclear reaction. A typical ion batch was 5.9 GBq of $[^{18}F]$fluoride at the end of bombardment for currents of 20 µA and irradiation times of 5 min. To recover the $[^{18}O]$water the ion batch of aqueous $[^{18}F]$fluoride was passed through an anion exchange resin (Sep-Pak® Light Waters Accell™ Plus QMA cartridge, preconditioned with 5 ml 1 M $K_2CO_3$ and 10 ml water for injection). $[^{18}F]$fluoride was eluted from the resin with a mixture of 40 µl 1 M $K_2CO_3$, 200 µl water for injection, and 800 µl DNA-grade $CH_3CN$ containing 10 mg Kryptofix®222. Subsequently, the aqueous $[^{18}F]K(Kryptofix222)F$ solution was carefully evaporated to dryness in vacuo. $[^{18}F]VI$ was prepared by treating the tosylate precursor (1.3 mg, 2.1 µmol) VIa with the carefully dried $[^{18}F]K(Kryptofix222)F$ residue in DNA-grade $CH_3CN$ (1 ml) at 84° C. for 5 min. Then $CH_3CN$ was evaporated in vacuo at 50° C. After cooling to rt the crude reaction mixture was passed through a Waters Sep-Pak® Light C18 cartridge with water for injection (10 mL). The cartridge was washed with additional water for injection (10 ml), followed by elution of the $[^{18}F]VI$ raw product with ethanol (1.5 ml). The ethanolic solution was fractionised using a semiautomatical radio-RP-HPLC procedure (conditions: flow 2 ml/min, λ=254 nm; eluents: A=$CH_3CN/H_2O$/TFA, 950/50/1, B=$CH_3CN/H_2O$/TFA, 50/950/1; Nucleosil 100 C18 5µ column (250×4.6 $mm^2$) with corresponding precolumn (20×4.6 $mm^2$); eluent B from 70% to 10% in 35 min, from 10% to 70% in 5 min) resulting in $[^{18}F]VI$ with radiochemical yields of 32% (decay-corrected) and radiochemical purities >90% (Retention time $R_t$=26 min). The determined specific radioactivity was 48 GBq/µmol at the end of synthesis (EOS). The time of synthesis and purification was 82 min from the end of bombardment (EOB). The absolute radiochemical yield was 1109 MBq at the EOS. Chemical identity of $[^{18}F]VI$ was proved by RP-HPLC and coinjection of $[^{18}F]VI$ and nonradioactive counterpart VI.

For in vivo experiments, the $[^{18}F]VI$ fraction was collected in 0.5 ml 8.4% sodium bicarbonate solution and dried in vacuo. Finally, $[^{18}F]VI$ was diluted in saline to reconstitute injectable doses with radioactivity concentrations of 70 MBq/ml.

[b]Radiosynthesis was carried out using a modified automated PET Tracer Synthesizer TRACERLab $FX_{FDG}$ (GE Functional Imaging GmbH). The recorded data were processed by the TRACERLab FDG software (GE Functional Imaging GmbH).

Separation of the radiosynthesised and unlabelled compounds, analyses of the radiochemical yields and radiochemical purities as well as specific activities were performed by a gradient radio-HPLC system composed of a RP-HPLC Nucleosil column 100 C-18 5μ 250×4.6 mm², a corresponding 20×4.6 mm² precolumn, a Knauer K-500 and a Latek P 402 pump, a Knauer K-2000 UV-detector (wavelength 254 nm) and a Crismatec Na(Tl) Scintibloc 51 SP51 gamma detector. Sample injection was carried out using a Rheodyne injector block (type 7125 incl. 200 μl loop). The recorded data were processed by the NINA radio-HPLC software, version 4.9 (GE Functional Imaging GmbH, Germany).

2.2 SPECT-compatible CbRs (eg. [$^{123}$I]1, [$^{123}$I]2, [$^{99m}$Tc]3 etc.)

2.2.1 Radiosynthesis of (S)-1-(4-[$^{125}$I]iodobenzyl)-5-(1-[2-(phenoxymethyl)pyrrolidinyl]sulfonyl)isatin [$^{125}$I]1

In a conical glas vial 0.56 mg (0.725 μmol) (S)-5-(1-[2-(phenoxymethyl)pyrrolidinyl]sulfonyl)-1-(4-(tributylstannyl)benzyl)-isatin Ia in 100 μl ethanol were added to a solution of 4 μl [$^{125}$I]NaI (approx. 14 MBq) in 0.05 N NaOH and 4 μl 0.05 M H$_3$PO$_4$. The radiosynthesis was started by adding 0.25 mg (1.095 μmol) chloramine-T hydrate (CAT) in 25 μl 0.1 M K$_2$HPO$_4$ (pH 7.36). The reaction mixture was vortexed and allowed to stand 5 min at RT. The resulting reaction suspension was diluted with 50 μl ethanol and was injected onto a gradient radio-RP-HPLC-chromatograph with a Nucleosil 100 column (C-18 5μ 250×4.6 mm) with a corresponding precolumn (20×4.6 mm) and combined γ-/UV-detectors to isolate the radiolabeled product [$^{125}$I]1. Radiochemical yield: 90%. Radiochemical purity: >95%. Calculated specific activity: 0.134 GBq/μg. HPLC-conditions: eluent A: CH$_3$CN/H$_2$O/ TFA 950/50/1, eluent B: CH$_3$CN/H$_2$O/TFA 50/950/1; time-program: isocratic run with 37% of eluent B; flow: 2.5 ml/min, λ:254 nm, R$_f$(product): 17.7 min.

Quality Control

200 μl of the product fraction was re-injected onto the HPLC column. The quality control did not show any impurities within the γ-range. Only the injection peak was detectable within the UV-range. HPLC-conditions: eluent A: CH$_3$CN/H$_2$O/TFA 950/50/1, eluent B: CH$_3$CN/H$_2$O/TFA 50/950/1; time-program: eluent B from 50% to 20% within 20 min, eluent B 20% for 10 min, eluent B from 20% to 50% within 10 min; flow: 2.5 ml/min; λ: 254 nm; R$_f$(product): 17.2 min.

Reference Control

The radioiodinated product [$^{125}$I]1 was verified by concentrating 150 μl of the isolated γ-fraction with 50 μl of a solution of the non-radioactive reference compound 1 in methanol (c=1 mg/ml methanol). The concentrated 200 μl mixture was again injected onto the HPLC column. Both the radiolabeled product and the non-radioactive reference standard corresponded to each other. HPLC-conditions: see Quality control; R$_f$(product): 16.9 min.

Scheme 12: CbRs of the invention

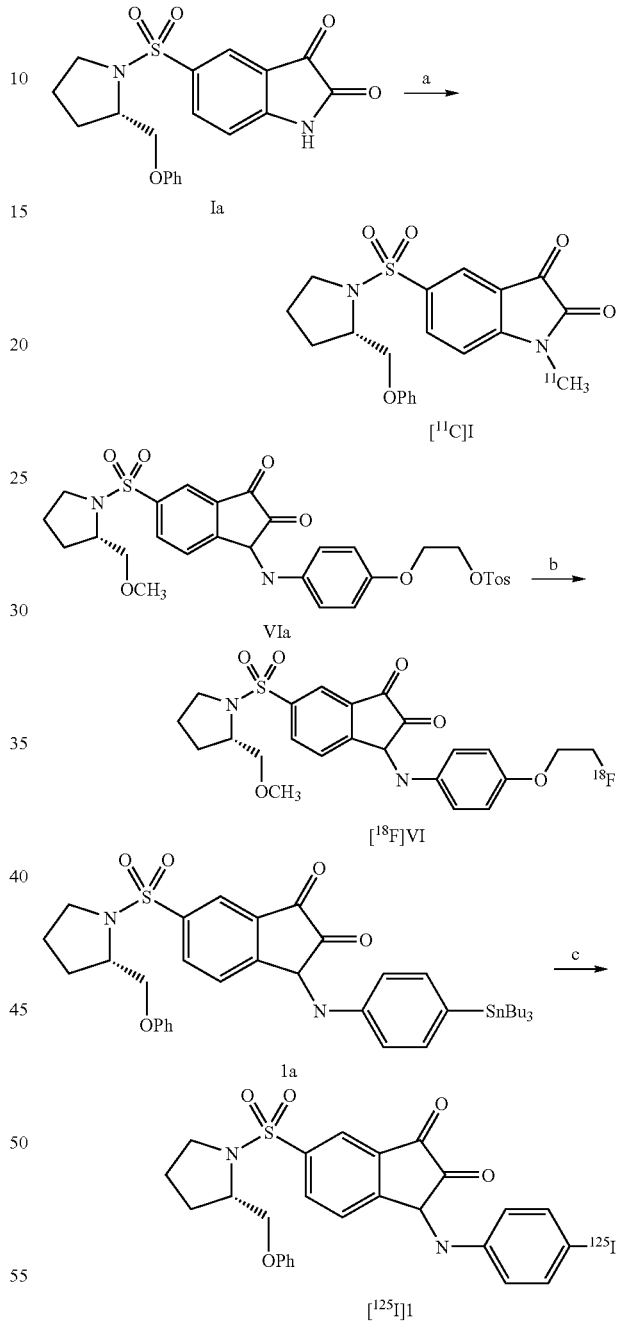

(a) NaH, [$^{11}$C]CH$_3$I, DMF; (b) [$^{18}$F]K(Kryptofix222)F, CH$_3$CN, (c) [$^{125}$I]NaI, chloramine-T, buffer.

3. Caspase Inhibition Assay

The inhibition of recombinant human caspase 3 by twentythree isatin sulfonamides (twenty of those representing new satin derivatives) has been assessed by using standard fluorometric assays [21a].

Recombinant full-length human caspase-3 was purified as described previously [21b]. The caspase-3 substrate Ac-DEVD-AMC (Ac-Asp-Glu-Val-Asp-AMC, $K_M$=9.7 mM±1 mM) was purchased from Alexis Biochemicals (Switzerland) and dissolved in a buffer consisting of 140 mM NaCl, 2.7 mM KCl, and 10 mM $KH_2PO_4$. Enzyme assays were performed in a 200 μl volume at 37° C. in reaction buffer containing 0.1% CHAPS, 50 mM KCl, 5 mM β-mercaptoethanol, 25 mM HEPES (pH 7.5) and nonradioactive isatins in DMSO each in single doses (end concentrations 500 μM, 50 μM, 5 μM, 500 nM, 50 nM, 5 nM, 500 pM, 50 pM or 5 pM). Recombinant caspase-3 was diluted into the appropriate buffer to a concentration of 1 unit per assay (=0.5 pM, i.e. 100 pM substrate conversion after 10 min). After 10 min incubation time Ac-DEVD-AMC (end concentration 10 μM) was added and reacted for further 10 min. Reaction rates showing inhibitory activity of the nonradioactive model inhibitor were measured with a Fusion™ universal microplate analyzer (PerkinElmer) at excitation and emission wavelengths of 360 and 460 nm, respectively. The $IC_{50}$-values were determined by non-linear regression analysis using the XMGRACE program (Linux software) and converted into the corresponding Ki-values by the equation $K_i=IC_{50}/(1+[S]/K_M)$ assuming competitive inhibition by the isatin derivatives, where [S] is the concentration and $K_M$ is the Michaelis constant of substrate Ac-DEVD-AMC.

The resulting $K_{i(app)}$ values in table 7 show that the in vitro affinities of the modified and new isatin sulfonamides have been significantly improved compared with the compounds of structures I, Ia and IIa (Scheme1).

TABLE 7

Inhibition constants of N-1-alkylated isatin derivatives

| Inhibitor $R_1$ = | Inhibitor $R_2$ = | $K_{i(app)}$/nM[a] Caspase 3 | log D values[b] |
|---|---|---|---|
| Ph | H— (Ia) | 89 ([21]: $IC_{50}$ = 44 nM) | 2.23 |
| Ph | [c]$CH_3$— (Ia) | 124 ([20]: 15 nM) | 2.27 |
| Ph | [c]4-$CH_3O$—$C_6H_4$—$CH_2$— (III) | n.d. | 3.96 |
| Ph | [d]4-I—$C_6H_4$—$CH_2$— (1) | 3 | 5.08 |
| Ph | 4-$(CH_3)_3Si$—$C_6H_4$—$CH_2$— (1b) | 0.7 | 6.55 |
| Ph | 4-Br—$C_6H_4$—$CH_2$— (1c) | 3 | 4.82 |
| Ph | 4-HO—$C_6H_4$—$CH_2$ (IIIa) | 3 | 3.31 |
| Ph | 4-BnO—$C_6H_4$—$CH_2$— (IIIaa) | 6.9 | 5.62 |
| Ph | 4-TBDMSO—$C_6H_4$—$CH_2$ (IIIab) | 20 | 2.44 |
| Ph | 4-TosO$(CH_2)_2$O—$C_6H_4$—$CH_2$— (Va) | 17 | 5.05 |
| Ph | 4-Br$(CH_2)_2$O—$C_6H_4$—$CH_2$— (Vaa) | 25 | 4.73 |
| Ph | [c]4-F$(CH_2)_2$O—$C_6H_4$—$CH_2$— (V) | 0.4 | 4.19 |
| $CH_3$ | H— (IIa) | 77 ([20]: 60 nM) | 0.26 |
| $CH_3$ | [c]$CH_3$— (II) | 2 | 0.28 |
| $CH_3$ | [c]4-$CH_3O$—$C_6H_4$—$CH_2$— (IV) | 9 | 1.97 |
| $CH_3$ | [d]4-I—$C_6H_4$—$CH_2$— (2) | 11 | 3.09 |
| $CH_3$ | 4-$Bu_3Sn$—$C_6H_4$—$CH_2$— (2a) | 22 | 9.86 |
| $CH_3$ | 4-HO—$C_6H_4$—$CH_2$ (IVa) | 45 | 1.32 |
| $CH_3$ | 4-BnO—$C_6H_4$—$CH_2$— (IVaa) | 5 | 3.62 |
| $CH_3$ | 4-TBDMSO—$C_6H_4$—$CH_2$ (IVab) | 4 | 0.45 |
| $CH_3$ | 4-TosO$(CH_2)_2$O—$C_6H_4$—$CH_2$— (VIa) | 2 | 3.05 |

TABLE 7-continued

Inhibition constants of N-1-alkylated isatin derivatives

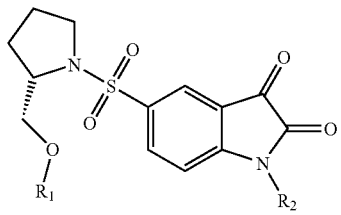

| Inhibitor R$_1$ = | Inhibitor R$_2$ = | K$_{i(app)}$/nM$^a$ Caspase 3 | log D values$^b$ |
|---|---|---|---|
| CH$_3$ | 4-Br(CH$_2$)$_2$O—C$_6$H$_4$—CH$_2$— (VIaa) | 13 | 2.73 |
| CH$_3$ | $^c$4-F(CH$_2$)$_2$O—C$_6$H$_4$—CH$_2$— (VI) | 36 | 2.20 |

$^a$K$_{i(app)}$ = IC$_{50}$/(1 + [S]/K$_M$) with [S] = 10 µM, K$_M$ = 9.7 mM ± 1.0 mM; S = Ac-DEVD-AMC
$^b$logD values calculated with ACD/Chemsketch Labs 6.00 (log D = log P at physiological pH (pH 7.4)
$^c$Non-radioactive target compounds of potential PET-compatible CbRs.
$^d$Non-radioactive target compounds of potential SPECT-compatible CbRs.

4. Cellular Caspase Assays

In the context of cellular apoptosis assays concentration- and time-dependent kinetics of mentioned CbRs and CbR-transporter conjugates are performed to evaluate the pharmacological inhibition of apoptosis in viable apoptotic cells (e.g. growth factor withdrawal-induced, drug-induced, or ionizing radiation-induced apoptosis in endothelial cells).

HUVEC (Human umbilical vein endothelial cells) were cultivated on gelatine (2%)-coated dishes in RPMI-1640 containing 15% bovine calf serum, 1% Pen/Strep/Amph, 1% Heparin and 0.05 mg/ml bovine pituitary extract (BPE) at 37° C. in 5% CO$_2$. Apoptosis was induced by growth factor withdrawal as previously described [39]. For caspase inhibition experiments, cells were pre-incubated for 30 min with the compounds in the indicated concentrations. The medium was then removed and replaced with RPMI-1640 without serum or BPE, and the cells were incubated in the presence or absence of the various inhibitor concentrations for 8 hours. All cells were then harvested in lysis buffer, incubated for 10 min on ice, and cell debris was removed by centrifugation at 14000 rpm at 4° C. for 10 min. Protein concentration was determined by the Pierce protein assay, and 30 µg cell lysate were loaded on 15% SDS-Page gels and transferred to Immobilon PVDF membranes. Western blots were performed with antibodies to active caspase-3 (Cell Signaling) and developed using ECL (Amersham).

A quantitative (pharmacological) inhibition of before mentioned target caspases with the non-radioactive PET- or SPECT-compatible CbRs of presented invention needs macroscopic amounts of the inhibitor, i.e. concentrations of caspase inhibitor that are definitely more than necessarily needed for molecular imaging purposes. Therefore, concentrations of inhibitor in the micromolar range (see FIGS. 1 and 2: Western blots of specific non-radioactive CbRs of the present invention) clearly demonstrate an incisive non-invasive imaging compatibility. The inhibition of caspase progression in the presence of compounds 2, II, IV, and VI, is already recognizable at 10 µM (FIGS. 1 and 2).

As can be seen from above the compounds of the present invention lead to PET- and SPECT-compatible CbR tracers with a 5-pyrrolidinylsulfonyl isatin skeletal structure that are able to target intracellular caspases, preferably the effector caspases 3 and 7. The potency of several new CbR reference substances (nonradioactive) has been proved in vitro using caspase inhibition assays. The new compounds comprise even higher affinities to caspase 3 compared with the compounds of structures I and IIa.

Thus the above CbRs enable a specific imaging of apoptosis leading to a enhanced efficacy and precision of therapeutic interventions (disease monitoring) and open new perspectives in many areas of disease management (therapy control).

5. In vivo experiments

Data Acquisition—PET.

PET was performed using a high-resolution dedicated small-animal PET system (32-module quadHIDAC; Oxford Positron Systems) which uses multiwire chamber detectors with submillimeter-resolution potency. For each data acquisition, up to two mice were placed on a heating pad to maintain a normal body temperature. The animals were anesthetised by inhalation of isoflurane (1.5%) and intravenously injected with approximately 7 MBq of each radiotracer in 100 µL isotonic as well as isohydric solution.

Acquisition Protocol—Biodistribution in WT Mouse (Nu/Nu)

A small-animal PET scan was performed with the quadHIDAC device to trace the in vivo biodistribution behavior of the PET-compatible CbR (S)-1-(4-(2[<18>F]fluoroethoxy)benzyl)-5-[1-(2-methoxymethylpyrrolidinyl)-sulfonyl]isatin [<18>F]VI. Immediately after i.v. injection of [<18>F]VI (A=7MBq, pH=8, A5=48 GBq/[mu]mol, V=100 [mu]1 in sodium bicarbonate buffered saline solution) data acquisition was started. List-mode data were acquired for 180 min and subsequently reconstructed into an image volume of 90×90×120 mm<3>, voxel size 0.4×0.4×0.4 mm<3>, using an iterative reconstruction algorithm (OPL-EM). As shown in FIG. 3, [<18>F]V1 was cleared 180 min p.i. from all peripheral organs. Radioactivity only remains in the bowels and in a hot spot nearby the liver which putatively can be assigned to the gall bladder. Mentioned hot spot remains even 6 h p.i. (data not shown). According to the here described invention [<18>F]VI is a PET-compatible CbR with corresponding pharmacokinetics, plasma clearance characteristics as well as imaging potency for the detection of locally upregulated caspase activity that is associated with induced apoptosis.

References

1. Kirschberg T A, VanDeusen C L, Rothbard J B, Yang M, Wender P A. Arginine-based molecular transporters: the synthesis and chemical evaluation of releasable taxol-transporter conjugates. *Org Lett* 2003; 5: 3459-62.

2. Rothbard J B, Garlington S, Lin Q, Kirschberg T, Kreider E, McGrane P L, Wender P A, Khavari P A. Conjugation of arginine oligomers to cyclosporin A facilitates topical delivery and inhibition of inflammation. *Nat Med* 2000; 6:1253-7.
3. Rothbard J B, Kreider E, VanDeusen C L, Wright L, Wylie B L, Wender P A. Arginine-rich molecular transporters for drug delivery: role of backbone spacing in cellular uptake. *J Med Chem* 2002; 45:3612-8.
4. Rothbard J B, Jessop T C, Lewis R S, Murray B A, Wender P A. Role of membrane potential and hydrogen bonding in the mechanism of translocation of guanidinium-rich peptides into cells. 2004; 126:9506-9507.
5. Kenis H, Van Genderen H, Bennaghmouch A, Rinia H A, Frederik P, Narula J, Hofstra L, Reutelingsperger C P. Cell surface expressed phosphatidylserine and Annexin A5 open a novel portal of cell entry. *J Biol Chem* 2004; Sep. 20 [Epub ahead of print]
6. Lahorte C M M, Vanderheyden J-L, Steinmetz N, Van de Wiele C, Dierckx R A, Slegers G. Apoptosis-detecting radioligands: current state of the art and future perspectives. *Eur J Nuci Med Mol Imaging* 2004; 31: 887-919.
7. Flotats A, Carrió I. Non-invasive in vivo imaging of myocardial apoptosis and necrosis. *Eur J Nuci Med* 2003; 30: 615-630.
8. Hofstra L, Liem I H, Dumont E A, et al. Visualization of cell death in vivo in patients with acute myocardial infarction. *Lancet* 2000; 356:209-212.
9. Blankenberg F G. Recent advances in the imaging of programmed cell death. *Curr Pharm Des* 2004; 10:1457-167.
10. Blankenberg F G, Tait J, Ohtsuki K, Strauss H W. Apoptosis: the importance of nuclear medicine. *Nucl Med Commun* 2000; 21:241-250.
11. Blankenberg F G, Katsikis P D, Tait J F, Davis R E, Naumovski L, Ohtsuki K, Kopiwoda S, Abrams M J, Darkes M, Robbins R C, Maecker H T, Strauss H W. In vivo detection and imaging of phosphatidylserine expression during programmed cell death. *Proc Natl Acad Sci USA* 1998; 95:6349-6354.
12. Kolodgie F D, Petrov A, Virmani R, Narula N, Verjans J W, Weber D K, Hartung D, Steinmetz N, Vanderheyden J L, Vannan M A, Gold H K, Reutelingsperger C P, Hofstra L, Narula J. Targeting of apoptotic macrophages and experimental atheroma with radiolabeled annexin V: a technique with potential for noninvasive imaging of vulnerable plaque. *Circulation* 2003; 108:3134-3139.
13. Narula J, Acio E R, Narula N, Samuels L E, Fyfe B, Wood D, Fitzpatrick J M, Raghunath P N et al. Annexin-V imaging for noninvasive detection of cardiac allograft rejection. *Nat. Med.* 2001; 7:1347-1352.
14. Thimister P W, Hofstra L, Liem I H, Boersma H H, Kemerink G, Reutelingsperger C P, Heidendal G A. In vivo detection of cell death in the area at risk in acute myocardial infarction. *J Nucl Med.* 2003; 44:391-396.
15. van de Wiele C, Lahorte C, Vermeersch H, Loose D, Mervillie K, Steinmetz N D, Vanderheyden J L, Cuvelier C A, Slegers G, Dierck R A. Quantitative tumor apoptosis imaging using technetium-99m-HYNIC annexin V single photon emission computed tomography. *J Clin Oncol* 2003; 21:3483-3487.
16. Concha N O, Abdel-Meguid S S. Controlling apoptosis by inhibition of caspases. *Curr Med Chem* 2002; 9:713-726.
17. Chapman J G, Magee W P, Stukenbrok H A, Beckius G E, Milici A J, Tracey W R. A novel nonpeptidic caspase-3/7 inhibitor, (S)-(+)-5-[1-(2-methoxymethylpyrrolidinyl)sulfonyl]isatin reduces myocardial ischemic injury. *Eur J Pharmacol* 2002; 456:59-68.
18. Haberkorn U, Kinscherf R, Krammer P H, Mier W, Eisenhut M. Investigation of a potential scintigrafic marker of apoptosis: radioiodinated Z-Val-Ala-DL-Asp(O-methyl)-fluoromethyl ketone. *Nucl Med Biol* 2001; 28: 793-798.
19. Talanian R V, Brady K D, Cryns V L. Caspases as targets for anti-inflammatory and anti-apoptotic drug discovery. *J Med Chem* 2000; 43:3351-71.
20. Lee D, Long S A, Adams J L, Chan G, Vaidya K S, Francis T A, Kikly K, Winkler J D, Sung C M, Debouck C, Richardson S, Levy M A, DeWolf W E Jr, Keller P M, Tomaszek T, Head M S, Ryan M D, Haltiwanger R C, Liang P H, Janson C A, McDevitt P J, Johanson K, Concha N O, Chan W, Abdel-Meguid S S, Badger A M, Lark M W, Nadeau D P, Suva L J, Gowen M, Nuttall M E. Potent and selective nonpeptide inhibitors of caspases 3 and 7 inhibit apoptosis and maintain cell functionality. *J Biol Chem* 2000; 275: 16007-14.
21. (a) Lee D, Long S A, Murray J H, Adams J L, Nuttall M E, Nadeau D P, Kikly K, Winkler J D, Sung C-M, Ryan M D, Levy M A, Keller P M, DeWolf W E. Potent and Selective Nonpeptide Inhibitors of Caspases 3 and 7. *J Med Chem* 2001; 44: 2015-2026: (b) Levkau B, Garton K J, Ferri N, Kloke K, Nofer J R, Baba H A, Raines E W, Breithardt G. xIAP induces cell-cycle arrest and activates nuclear factor-kappaB: new survival pathways disabled by caspase-mediated cleavage during apoptosis of human endothelial cells. *Circ Res* 2001, 88: 282-290.
22. Lee Dennis (US); Long Scott Allen (US). Sulfonyl isatin compounds and methods of blocking apoptosis therewith. SMITHKLINE BEECHAM CORP (US), U.S. Pat. No. 6,403,792, date of publication: Jun. 11, 2002.
23. Ell P J, Gambhir S S. *Nuclear Medicine in Diagnosis and Treatment.* Churchill Livingstone Edinburgh, 2004.
24. Welch M, Redvanly C S. *Handbook of Radiopharmaceuticals.* John Wiley & Sons, 2003
25. Bolton R. Isotopic methylation. *J Labelled Compds Radiopharm* 2001; 44; 701-736.
26. Hamacher K, Coenen H H. Efficient routine production of the $^{18}F$-labelled amino acid O-2-$^{18}F$ fluoroethyl-L-tyrosine. *Appl Radiat Isot* 2002; 57:853-6.
27. Wester H J, Herz M, Weber W, Heiss P, Senekowitsch-Schmidtke R, Schwaiger M, Stocklin G. Synthesis and radiopharmacology of O—(2-[$^{18}F$]fluoroethyl)-L-tyrosine for tumor imaging. *J Nucl Med* 1999; 40:205-12.
28. Lasne M-C, Perrio C, Rouden J, Barré L, Roeda D, Dolle F, Crouzel C. Chemistry of, $\beta^+$-emitting compounds based on fluorine-18. *Topics in Current Chemistry* 2002; 222: 201-258.
29. Knöchel A, Zwernemann O. Development of a no-carrier-added method for $^{18}F$-labelling of aromatic compounds by fluorodediazonation. *J Label Compd Radiopharm* 1996; 38:325-326.
30. Wilbur D S. Radiohalogenation of proteins: An overwiew of radionuclides, labelling methods and reagents for conjugate labelling. *Bioconjugate Chem* 1992; 3: 433-470.
31. Bolton R. Radiohalogen incorporation into organic systems. *J Labelled Compds Radiopharm* 2002; 45:485-528.
32. Schibli R, La Bella R, Alberto R, Garcia-Garayoa E, Ortner K, Abram U, Schubiger P A. Influence of the Denticity of Ligand Systems on the in Vitro and in Vivo Behaviour of $^{99m}Tc(1)$-Tricarbonyl complexes: a hint for the future functionalization of biomolecules, *Bioconjug Chem* 2000; 11:345-351.
33. Stichelberger A, Waibel R, Dumas C, Schubiger P A, Schibli R. Versatile synthetic approach to new bifunctional chelating agents tailor made for labeling with the fac-[M (CO)(3)](+) core (M=Tc, (99m)Tc, Re): synthesis, in vitro, and in vivo behavior of the model complex [M(APPA) (CO)(3)] (APPA=[(5-amino-pentyl)-pyridin-2-yl-methyl-amino]-acetic acid). *Nucl Med Biol* 2003; 30:465-70.
34. Schwochau K. Technetium. *Chemistry and Radiopharmaceutical Applications.* Wiley-VCH: Weinheim, 2000.
35. Schibli R, La Bella R, Alberto R, Garcia-Garayoa E, Ortner K, Abram U, Schubiger P A. Influence of the Denticity of Ligand Systems on the in Vitro and in Vivo Behaviour of $^{99m}$Tc(I)-Tricarbonyl complexes: a hint for the future functionalization of biomolecules, *Bioconjug Chem* 2000; 11:345-351.
36. Greenland W E, Howland K, Hardy J, Fogelman I, Blower P J. Solid-phase synthesis of peptide radiopharmaceuticals using Fmoc-N-epsilon-(hynic-Boc)-lysine, a technetium-binding amino acid: application to Tc-99m-labeled salmon calcitonin. *J Med Chem* 2003; 46:1751-7.
37. Zijlstra S, Gunawan J, Burchert W. Synthesis and evaluation of a $^{18}$F-labelled recombinant annexin-V derivative, for identification and quantification of apoptotic cells with PET. *Appl Radiat Isot* 2003; 58:201-7.
38. Holschbach M, Schüller M. A new and simple on-line method for the preparation of n.c.a. [$^{11}$C]methyl iodide. *Appl Radiat Isot* 1993; 44:779-780.
39. Levkau B, Raines E W, Clurmann B E, Herren B, Orth K, Roberts J M, Ross, R. Cleavage of p21Cip1NWaf1 and p27Kip1 mediates apoptosis in endothelial cells through activation of Cdk2: role of a caspase cascade. *Mol Cell* 1998, 1:553-63.

The invention claimed is:

1. A non-peptidyl CbR (Caspase binding Radioligand) or CbR-transporter conjugate that is a 5-pyrrolidinylsulfonyl isatin derivative having the formula 1,

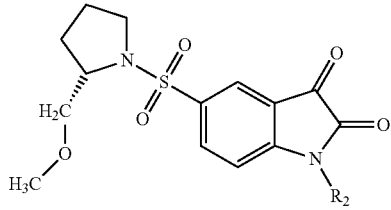

Formula 1 wherein, $R_2$ is an optionally substituted alkyl, heteroalkyl, aralkyl, heteroarylalkyl, carboxymethyl or methyloxycarbonylmethyl group, wherein the substituents are selected from F, I, Br, OH, $NH_2$, methylamino, methoxy, fluoroethyloxy, fluoropropyloxy, trimethylamino, nitro, tosylate, triflate, mesylate, diazonium $N_2^+$, 3-fluorobenzoyl, 4-fluorobenzoyl, 4-fluorophenyl, tributylstannyl, trimethylstannyl, trimethylsilyl, 2-hydrazino-pyridin-5-carbonyl; or a metal-chelator or a metal-chelator bound to an aralkyl, aminoalkyl, hydroxyalkyl or piperazin-1-carbonylmethyl group; and optionally additionally comprises a spacer, linker or molecular transporter selected from Annexin V, $PEG_{1-200}$, an oligopeptide, polyimide, polysaccharide, —NHC(O)—((CH$_2$)$_n$—NH—C(O))$_m$—, —O—((CH$_2$)$_n$—O)$_m$—, succinyl and 1,4-disubstituted 1,2,3-triazole units, wherein n=0-6 and m=1-200 and wherein $R_2$ can also contain an amino acid selected from histidine, lysine, tyrosine, cysteine, arginine and aspartic acid;

wherein $R_2$ is labelled with a positron-emitting non-metal radionuclide selected from C-11, N-13, and F-18.

2. The CbR or CbR-transporter conjugate according to claim 1, wherein $R_2$ is 3-(2'-[$^{11}$C]isopropyl)aminopropyl, [$^{11}$C]methyl, 3-[$^{11}$C]methylaminopropyl, [$^{11}$C]methyloxycarbonylmethyl, 4-[$^{11}$C]methyloxybenzyl, 4-(2-[$^{18}$F]fluorethyloxy)benzyl, 4-(3-[$^{18}$F]fluoropropyloxy)benzyl 4-[$^{11}$C]methyl-piperazin-1-carbonylmethyl, 4-(2'-[$^{11}$C]isopropyl)piperazin-1-carbonylmethyl, 4-(3-[$^{18}$F]fluoropropyl)piperazin-1-carbonylmethyl), 6-[$^{18}$F]fluoro-2-picolyl-, 2- or 6-[$^{18}$F]fluoro-3-picolyl, 2-[$^{18}$F]fluoro-4-picolyl; or [$^{11}$C]methyloxycarbonylmethyl.

3. A diagnostic composition comprising a non-peptidyl CbR (Caspase binding Radioligand) or CbR-transporter conjugate according to claim 1 and a carrier.

* * * * *

UNITED STATES PATENT AND TRADEMARK OFFICE
CERTIFICATE OF CORRECTION

PATENT NO. : 8,440,841 B2
APPLICATION NO. : 11/794878
DATED : May 14, 2013
INVENTOR(S) : Kopka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 624 days.

Signed and Sealed this
Eighth Day of September, 2015

Michelle K. Lee
*Director of the United States Patent and Trademark Office*